US010245281B2

(12) United States Patent
Cool et al.

(10) Patent No.: US 10,245,281 B2
(45) Date of Patent: Apr. 2, 2019

(54) GLYCOSAMINOGLYCANS

(71) Applicant: Agency for Science, Technology and Research, Singapore (SG)

(72) Inventors: Simon Cool, Singapore (SG); Victor Nurcombe, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 336 days.

(21) Appl. No.: 14/814,680

(22) Filed: Jul. 31, 2015

(65) Prior Publication Data

US 2015/0328251 A1 Nov. 19, 2015

Related U.S. Application Data

(62) Division of application No. 13/617,740, filed on Sep. 14, 2012, now abandoned.

(30) Foreign Application Priority Data

Sep. 16, 2011 (SG) .................................. 201106706

(51) Int. Cl.
| | | |
|---|---|---|
| *A61P 9/10* | (2006.01) | |
| *A61K 31/727* | (2006.01) | |
| *C08B 37/00* | (2006.01) | |
| *A61K 31/737* | (2006.01) | |
| *A61L 27/34* | (2006.01) | |
| *A61L 27/54* | (2006.01) | |
| *A61K 38/18* | (2006.01) | |

(52) U.S. Cl.
CPC .......... *A61K 31/727* (2013.01); *A61K 31/737* (2013.01); *A61K 38/1866* (2013.01); *A61L 27/34* (2013.01); *A61L 27/54* (2013.01); *A61P 9/10* (2018.01); *C08B 37/0078* (2013.01); *A61L 2300/412* (2013.01)

(58) Field of Classification Search
CPC ............ C08B 37/0075; C08B 37/0078; A61K 31/737; A61L 27/20; A61L 27/34; A61L 27/3629; A61L 27/3633; A61L 27/54; A61L 27/507; A61L 2300/236; A61L 2300/412; A61L 2300/414
See application file for complete search history.

(56) References Cited

U.S. PATENT DOCUMENTS

| 5,986,168 A | 11/1999 | Noishiki | |
|---|---|---|---|
| 9,498,497 B2 | 11/2016 | Chang et al. | |
| 2004/0141945 A1* | 7/2004 | Yura | A61K 31/726 424/85.1 |
| 2013/0045249 A1 | 2/2013 | Cool et al. | |
| 2013/0071443 A1 | 3/2013 | Cool et al. | |
| 2014/0106012 A1 | 4/2014 | Levin et al. | |

FOREIGN PATENT DOCUMENTS

| WO | WO-2010/029278 A2 | 3/2010 |
|---|---|---|
| WO | WO-2010/030244 A1 | 3/2010 |

OTHER PUBLICATIONS

Otrock, Z. et al "Understanding the biology of angiogenesis . . . " Blood Cells, Molecules and Diseases (2007) vol. 39, pp. 212-220.*
Fuster, M. et al "Endothelial heparan sulfate in angiogenesis" Prog. Mol. Biol. Transl. Sci., vol. 93, pp. 179-212. (Year: 2010).*
Ashikari-Hada, S. et al., Heparin Regulates Vascular Endothelial Growth Factor$_{165}$-dependent Mitogenic Activity, Tube Formation, and Its Receptor Phosphorylation of Human Endothelial Cells, The Journal of Biological Chemistry, 280(36):31508-31515 (2005).
Chipperfield, H. et al., Heparan sulfates isolated from adult neural progenitor cells can direct phenotypic maturation, Int.J.Dev.Biol., 46:661-60 (2002).
Cool, S.M. and Nurcombe, V., Heparan Sulfate Regulation of Progenitor Cell Fate, Journal of Cellular Biochemistry, 99:1040-1051 (2006).
Dager, W.E. et al., Heparin-Induced Thrombocytopenia: Treatment Options and Special Considerations, Pharmacotherapy, 27(4):564-587 (2007).
Dombrowski, C. et al., Heparan Sulfate Mediates the Proliferation and Differentiation of Rat Mesenchymal Stem Cells, Stem Cells and Development, 18(4):661-670 (2009).
Fairbrother, W. et al., Solution structure of the heparin-binding domain vascular endothelial growth factor, Structure, 6:637-648 (1998).
Haupt, L.M. et al., The Heparan Sulfate Proteoglycan (HSPG) Glypican-3 Mediates Commitment of MC3T3-E1 Cells Toward Osteogenesis, Journal of Cellular Physiology, 220:780-791 (2009).
Jackson, R.A. et al., Coordinated fibroblast growth factor and heparan sulfate regulation of osteogenesis, Gene, 379:79-91 (2006).
Krilleke, D. et al., Molecular Mapping and Functional Characterization of the VEGF164 Heparin-binding Domain, The Journal of Biological Chemistry, 282(38):28045-28056 (2007).
Kusmer, K., Third Preemie Dies From Drug Overdose at Indiana Hospital, Press Release (2006).
Lever, R. and Page, C.P., Novel Drug Development Opportunities for Heparin, Nature Reviews Drug Discovery, 1:140-148 (2002).
Manton, K.J. et al., Bone-Specific Heparan Sulfates Induce Osteoblast Growth Arrest and Downregulation of Retinoblastoma Protein, Journal of Cellular Physiology, 209:219-229 (2006).
Manton, K.J. et al., Disruption of Heparan and Chondroitin Sulfate Signaling Enhances Mesenchymal Stem Cell-Derived Osteogenic Differentiation via Bone Morphogenetic Protein Signaling Pathways, Stem Cells, 25:2845-2854 (2007).

(Continued)

*Primary Examiner* — Leigh C Maier
(74) *Attorney, Agent, or Firm* — Choate, Hall & Stewart LLP; Kristen C. Buteau; Nicholas J. Pace

(57) ABSTRACT

Heparan sulphate HS7 is disclosed, together with the use of HS7 in the growth and/or development and/or regeneration of tissue.

15 Claims, 20 Drawing Sheets

Specification includes a Sequence Listing.

(56) References Cited

OTHER PUBLICATIONS

Murali, S. et al., Comparative Assessment of the Effects of Gender-specific Heparan Sulfates on Mesenchymal Stem Cells, The Journal of Biological Chemistry, 286(20):17755-17765 (2011).

Murali, S. et al., Purification and Characterization of Heparan Sulfate From Human Primary Osteoblasts, Journal of Cellular Biochemistry, 108:1132-1142 (2009).

Nurcombe, V. and Cool, S.M., Heparan Sulfate Control of Proliferation and Differentiation in the Stem Cell Niche, Critical Reviews in Eukaryotic Gene Expression, 17(2):159-171 (2007).

Nurcombe, V. et al., Temporal and functional changes in glycosaminoglycan expression during osteogenesis, J Mol Hist, 38:469-481 (2007).

Simons, M. et al., Clinical Trials in Coronary Angiogenesis: Issues, Problems, Consensus: An Expert Panel Summary, Circulation, 102:e73-e86 (2000).

Singh, S. et al., The enhancement of VEGF-mediated angiogenesis by polycaprolactone scaffolds with surface cross-linked heparin, Biomaterials, 32:2059-2069 (2011).

Van Der Laan, A.M. et al., Targeting angiogenesis to restore the microcirculation after reperfused MI, Nature Reviews Cardiology, 6:515-523 (2009).

Wang, C. et al., A polysaccharide isolated from the medicinal herb *Bletilla striata* induces endothelial cells proliferation and vascular endothelial growth factor expression in vitro, Biotechnology Letters, 28:539-543 (2006).

Xu, D. et al., Heparan Sulfate Regulates $VEGF_{165}$- and $VEGF_{121}$-mediated Vascular Hyperpermeability, The Journal of Biological Chemistry, 286(1):737-745 (2011).

Ylä-Herttuala, S. et al., Vascular Endothelial Growth Factors, Journal of the American College of Cardiology, 49(10):1015-1026 (2007).

Zieris, A. et al., FGF-2 and VEGF functionalization of starPEG-heparin hydrogels to modulate biomolecular and physical cues of angiogenesis, Biomaterials, 31:7985-7994 (2010).

* cited by examiner

Lane 1: VEGF
Lane 2: VEGF+HS7
Lane 3: VEGF+ HS7$^{Neg}$
Labe 4: VEGF+ HS$^{Celsus}$

B

GLYCOSAMINOGLYCANS

PRIORITY CLAIM

This application claims priority to Singapore Patent Application No. SG 201106706-3 filed Sep. 16, 2011, the entire contents of which are incorporated herein by reference.

SEQUENCE LISTING

In accordance with 37 CFR 1.52(e)(5), a Sequence Listing in the form of a text file (entitled "sequence_listing.txt," created on Sep. 13, 2012, and 4 kilobytes in size) is incorporated herein by reference in its entirety.

FIELD OF THE INVENTION

The present invention relates to glycosaminoglycans capable of binding to VEGF, including their isolation and identification, and the use of the isolated glycosaminoglycans in the growth and/or development and/or regeneration of tissue.

BACKGROUND TO THE INVENTION

Ischemic heart and vascular diseases are the leading cause of death worldwide, accounting for more than 7 million deaths globally and 1 in 5 deaths in Singapore each year[1]. Diseases, such as myocardial infarction, stroke and limb ischemia, occur due to blockage of arteries and reduced blood supply to heart muscle, brain, and limb, respectively. Novel pro-angiogenic treatments aimed at developing collateral blood flow to limit tissue damage following an ischemic event have attracted much attention[2,3]. Angiogenesis is principally mediated by growth factors, most notably VEGF (in particular the $VEGF_{165}$ isoform) that exerts angiogenic activity by binding and activating VEGF receptor 2, one of the two transmembrane receptor tyrosine kinases expressed on blood endothelial cells; so triggering downstream mitogen-activated signals[4-7]. Due to its potent pro-angiogenic effects, VEGF has been trialled in clinical applications, but the outcomes have so far been disappointing[2,3,8]. The major obstacle is that this soluble peptide growth factor is unstable in physiological environments and rapidly degrades, and has to be administered at high (and excessive) dose that causes unwanted side effects. It is also expensive to produce. As such, an effective, stable, and less expensive medication is in high demand to achieve more rapid and successful restoration of blood supply to degenerative sites.

Whilst pro-angiogenesis therapies hold great promise for treating myocardial infarction, limb and other ischemic vascular diseases with high mortality, VEGF therapy for the treatment of ischemic disease has been questioned as therapeutic concentrations of soluble proteins are difficult to maintain at ischemic sites, and exogenous growth factors easily lose activity while being overdosed. Thus, new, effective, stable and cheaper medication for accomplishing VEGF-mediated angiogenesis is required.

The biomedical community has recently discovered the importance of HS and its pro-angiogenic action with VEGF. HS is a variably sulfated, linear polysaccharide composed of repeating disaccharide units of glucoronic acid (GlcA) and glucosamine (GlcN), and plays essential roles in controlling cell phenotype and tissue development[9,10]. Certain HS species, together with the likes of neuropillin-1, are required to form a complex with VEGF ligand and receptor to stabilise and enhance the $VEGF_{165}$-VEGFR2 interaction[4]. Specifically, HS binds to the 55-residue COOH-terminal amino acid sequence of $VEGF_{165}$, and regulates $VEGF_{165}$-mediated endothelial proliferation, tube formation, as well as vascular hyperpermeability[5,6]. In combination with polymer-based biomaterials, heparin has shown favourable ability in maintaining a sustained release of VEGF and producing localised vascularisation[11,12]. However, heparin is not suitable to stimulating angiogenesis in clinical applications. First, this highly charged HS species has notable anti-coagulant effects that cause serious adverse events such as haemorrhage (bleeding), thrombocytopenia, and hyperkalemia[13,14]. Overdoses of heparin have also been reported and are fatal[15]. Second, instead of selectively binding pro-angiogenic factors, heparin and mixtures of HS variants ubiquitously bind a variety of other soluble growth factors; given their inherent lack of specificity. Some of these nonspecific bindings may bring forward unpredictable effects that may antagonise the fundamental process needed for controlled angiogenesis.

SUMMARY OF THE INVENTION

In one aspect the present invention provides the heparan sulphate HS7, which may be provided in isolated or substantially purified form.

In some embodiments HS7 is capable of binding SEQ ID NO:1, optionally with a $K_D$ of less than 100 µM, or one of less than 50 µM, 40 µm, 30 µM, 20 µM, or 10 µM.

HS7 may be obtained by a method comprising:
(i) providing a solid support having polypeptide molecules adhered to the support, wherein the polypeptide comprises a heparin-binding domain having the amino acid sequence of SEQ ID NO:1;
(ii) contacting the polypeptide molecules with a mixture comprising glycosaminoglycans such that polypeptide-glycosaminoglycan complexes are allowed to form;
(iii) partitioning polypeptide-glycosaminoglycan complexes from the remainder of the mixture;
(iv) dissociating glycosaminoglycans from the polypeptide-glycosaminoglycan complexes;
(v) collecting the dissociated glycosaminoglycans.

In some embodiments the mixture comprising glycosaminoglycans is a heparan sulphate preparation obtained from porcine mucosa.

In another aspect of the present invention a composition comprising HS7 is provided. In some embodiments a pharmaceutical composition or medicament comprising HS7 is provided. In some embodiments the pharmaceutical composition or medicament further comprises VEGF protein. In some aspects of the present invention the pharmaceutical composition or medicament is provided for use in a method of medical treatment.

In a further aspect of the present invention HS7 is provided for use in a method of medical treatment. In some embodiments the method of treatment involves the stimulation or promotion of the growth of blood vessels.

In another aspect of the present invention the use of HS7 in the manufacture of a medicament for the treatment of a disease, condition or injury to tissue is provided, wherein the method involves the stimulation or promotion of the growth of blood vessels.

In a further aspect of the present invention a method of treating a disease, condition or injury to tissue in a patient is provided, the method comprising administration of a therapeutically effective amount of HS7 to the patient. In some embodiments the method involves the stimulation or promotion of the growth of blood vessels in the patient. In some embodiments the method further comprises administering VEGF protein to the patient.

In some embodiments methods of treatment comprise administering HS7 to tissue at or surrounding a wound or location on/in the patient's body at which blood vessel growth is required.

In a further aspect of the present invention a method of treating a disease, condition or injury to tissue in a patient is provided, the method comprising surgically implanting a biocompatible implant or prosthesis, which implant or prosthesis comprises a biomaterial and HS7, into tissue of the patient at or surrounding the site of the disease, condition or injury.

In another aspect of the present invention a biocompatible implant or prosthesis comprising a biomaterial and HS7 is provided.

In a further aspect of the present invention a method of forming a biocompatible implant or prosthesis is provided, the method comprising the step of coating or impregnating a biomaterial with HS7.

In another aspect of the present invention a method of promoting growth of blood vessels is provided, the method comprising administering HS7 to vascular cells or to vascular tissue. In some embodiments the vascular cells or vascular tissue are contacted with HS7 in vitro. In other embodiments the vascular cells or vascular tissue are contacted with HS7 in vivo.

BRIEF DESCRIPTION OF THE DRAWING

Embodiments and experiments illustrating the principles of the invention will now be discussed with reference to the accompanying figures of the drawing in which:

FIG. 6. Table showing percentage normalised disaccharide composition of Celsus HS, HS7+ (HS7 retained), HS7− (HS7 not retained) and HS3. Values indicated in bold are the normalised disaccharide composition of individual digests. Error values are indicated directly below. The error was calculated using student t-test at the 95% confidence level using the duplicate analyses of two digests.

DESCRIPTION OF CERTAIN EMBODIMENTS OF THE INVENTION

The present invention concerns the novel heparan sulphate HS7, which has been isolated by the inventors. Isolated HS7 is heparin-free and provides high activating affinity for VEGF.

Applications of HS7 include:

1. Providing agents capable of being used in medical treatment as an alternative to exogenously applied VEGF, whilst optionally being capable of sequestering endogenous VEGF at sites of ischemia.

2. As an adjuvant that, when bound to VEGF, reduces the amounts of exogenous VEGF required to promote angiogenesis, wherein the HS7 optionally:
   (a) protects and/or potentiates the effects of VEGF,
   (b) acts as a reservoir for VEGF,
   (c) contributes to the release of bioavailable VEGF at infarct sites, and/or
   (d) provides for a longer term sustained effect of VEGF.

HS7

The present invention relates to HS7, which is obtainable by methods of enriching mixtures of compounds containing one or more glycosaminoglycans (GAGs) that bind to a polypeptide corresponding to a heparin-binding domain of VEGF. The enrichment process may be used to isolate HS7.

The present invention also relates to mixtures of compounds enriched with HS7, and methods of using such mixtures.

Figure 2:
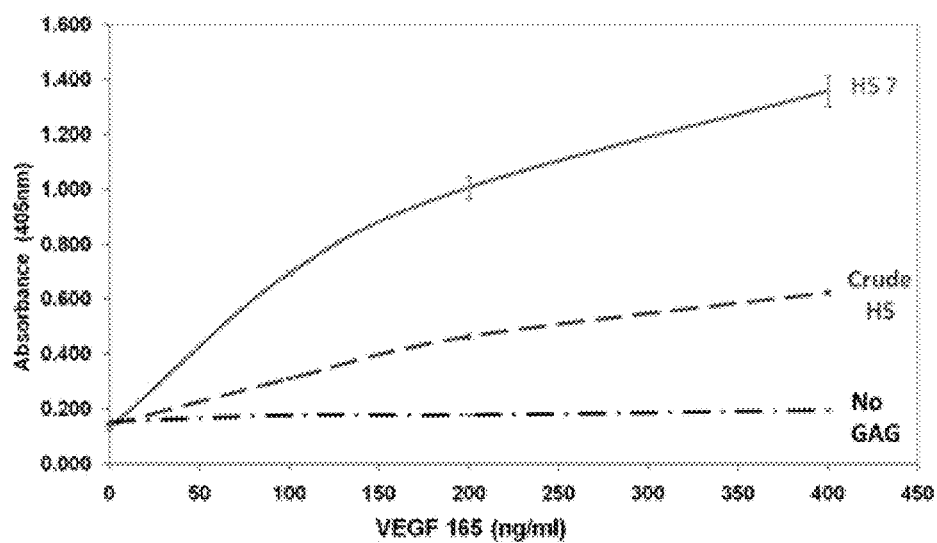
FIG. 2. (A) GAG-ELISA comparing the binding affinity of HS7 and $HS^C$ for $VEGF_{165}$; (B) CAM assay for testing the pro-angiogenic activity of VEGF ($VEGF_{165}$) and HS7 on the chicken embryo chorioallantoic membrane. Representative photos and intensities are given.
Figure 2:
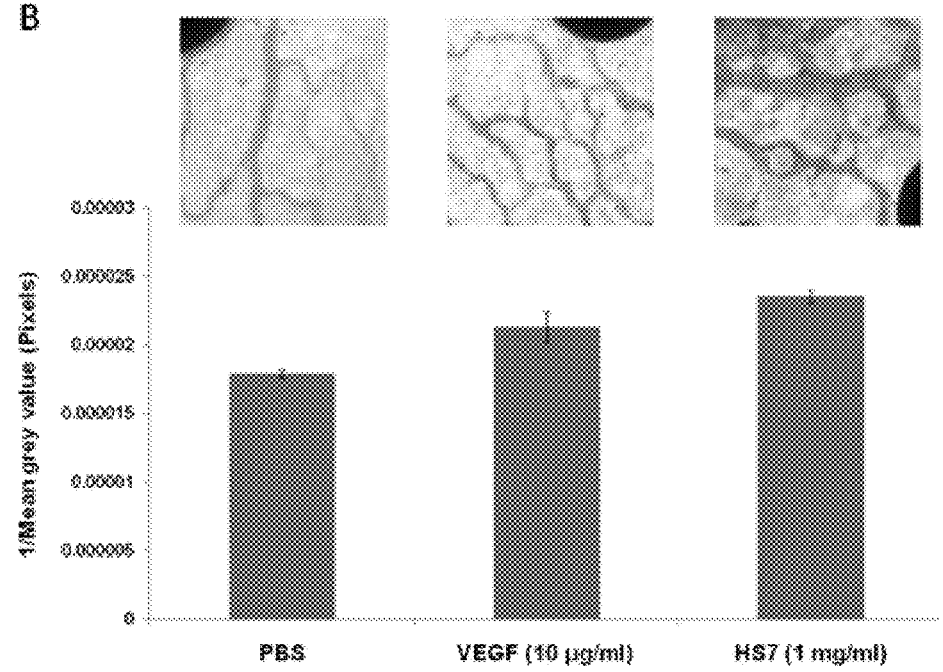
Figure 3:
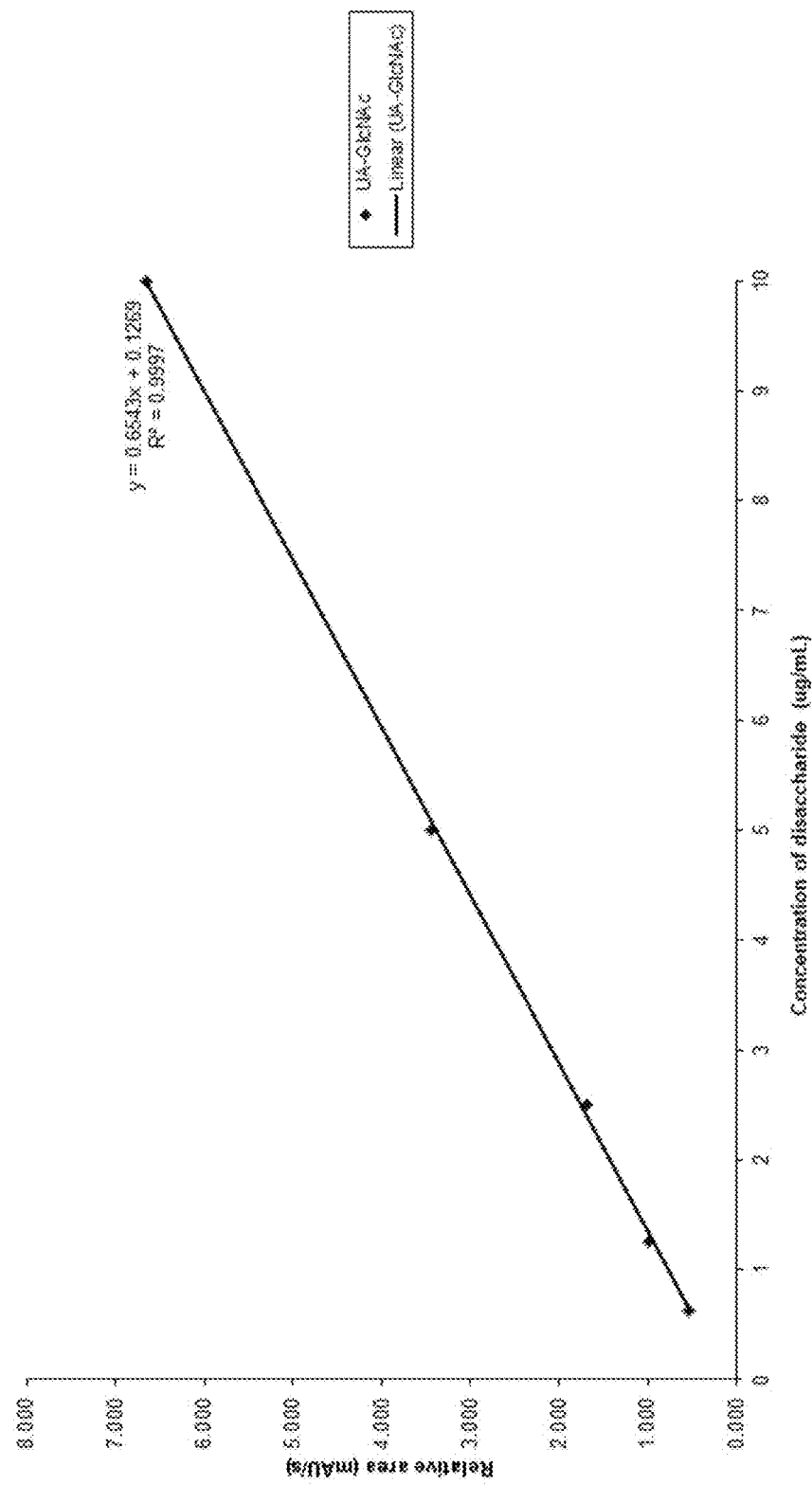
FIG. 3. Charts showing data from capillary electrophoresis of heparin disaccharide standards. (A) UA-GlcNAc, (B) UA-GlcN,6S (lower line) and US,2S-GlcN (upper line), (C) US,2S-GlcNS (upper line at 10 µg/mL), US-GlcNS,6S (lower line at 10 µg/mL), US,2S-GlcNAc,6S (middle line at 10 µg/mL), (D) UA,2S-GlcN,6S, (E) UA-GlcNS (middle line at 10 µg/mL), UA,2S-GlcNAc (lower line at 10 µg/mL), UA-GlcNAc,6S (upper line at 10 µg/mL), (F) UA,2S-GlcNS,6S.
Figure 3:
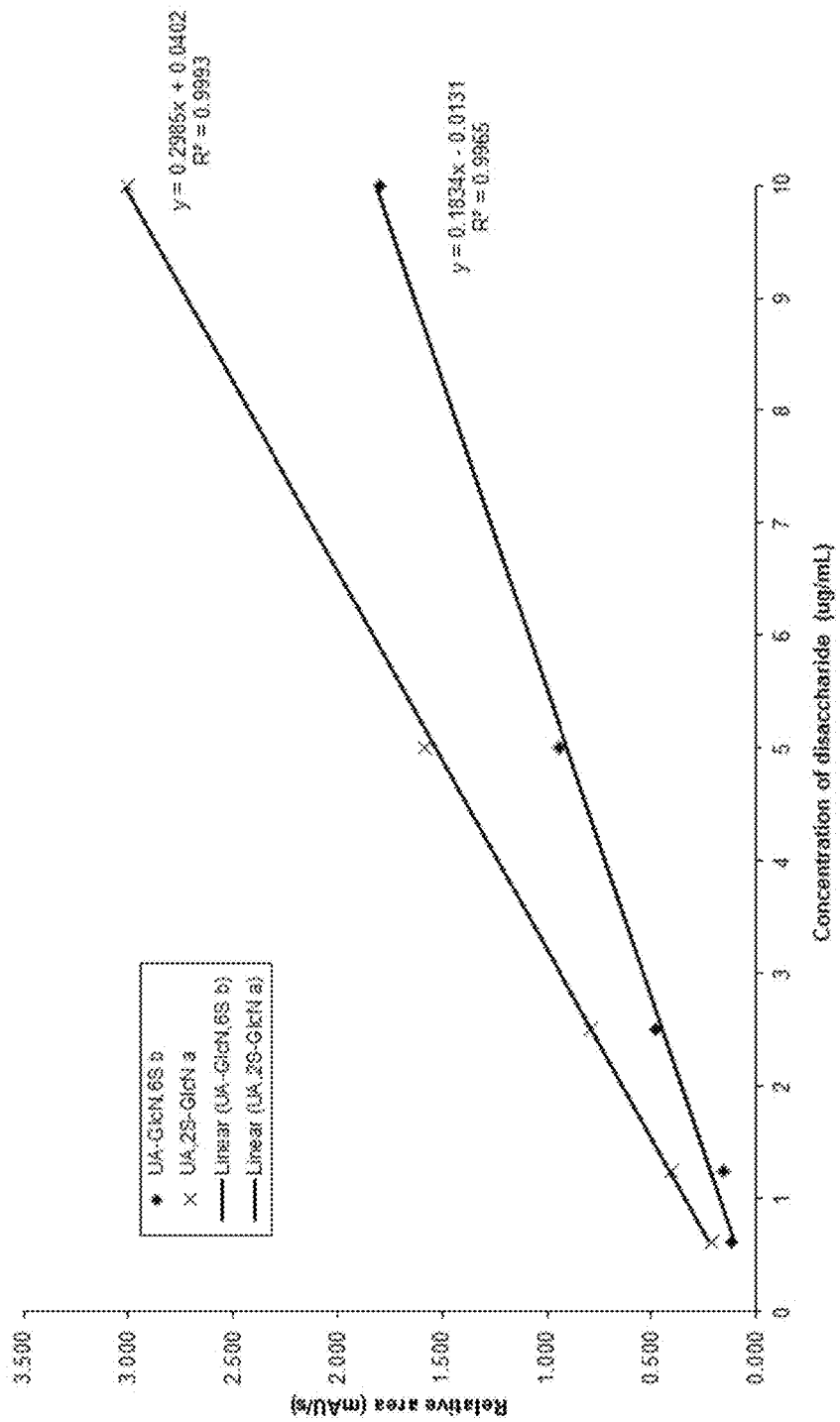
Figure 3:
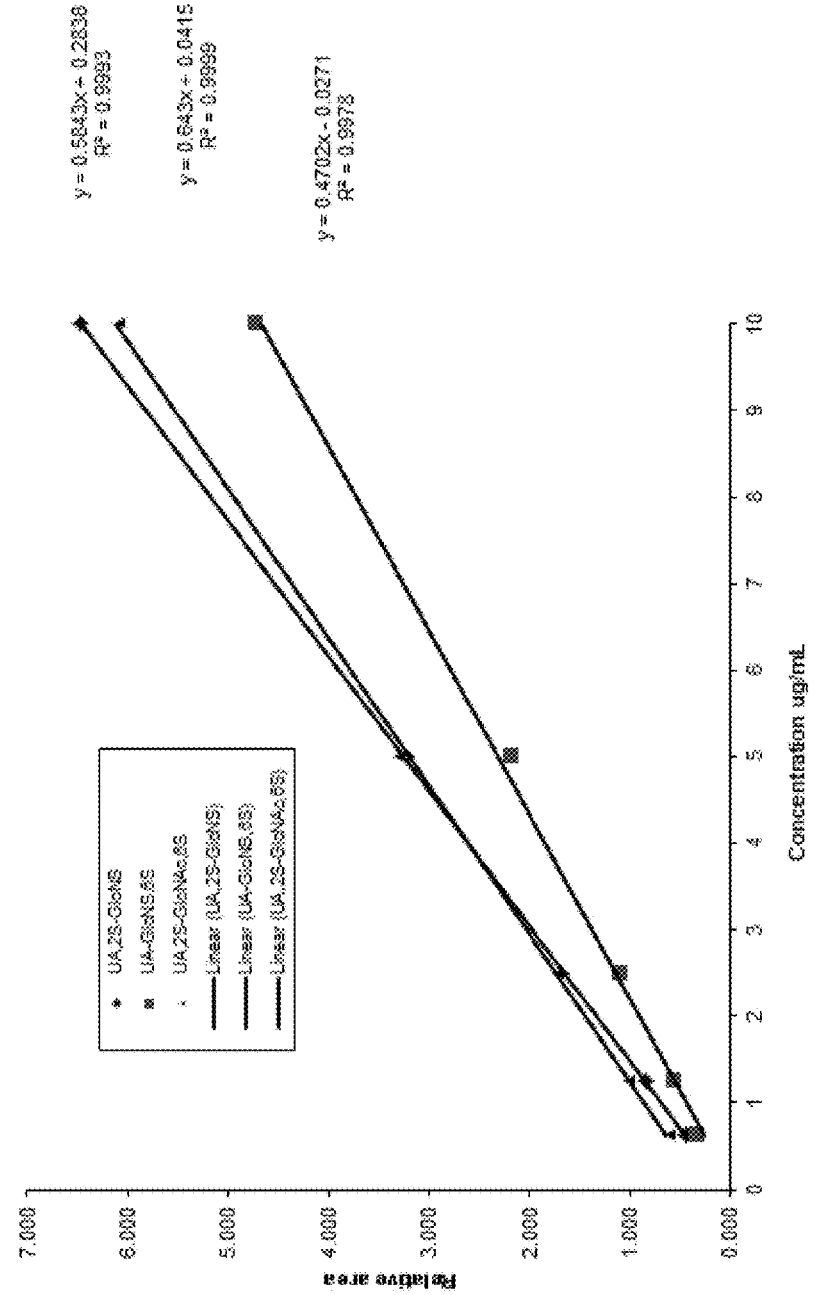
Figure 3:
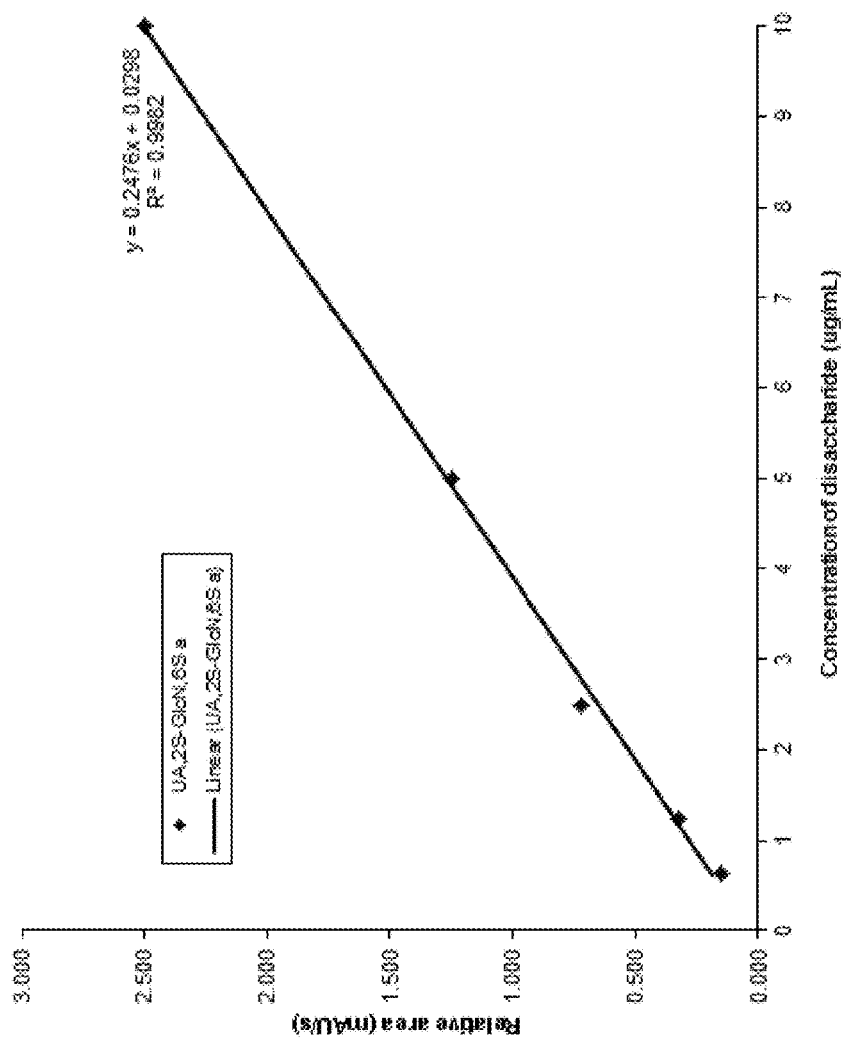
Figure 3:
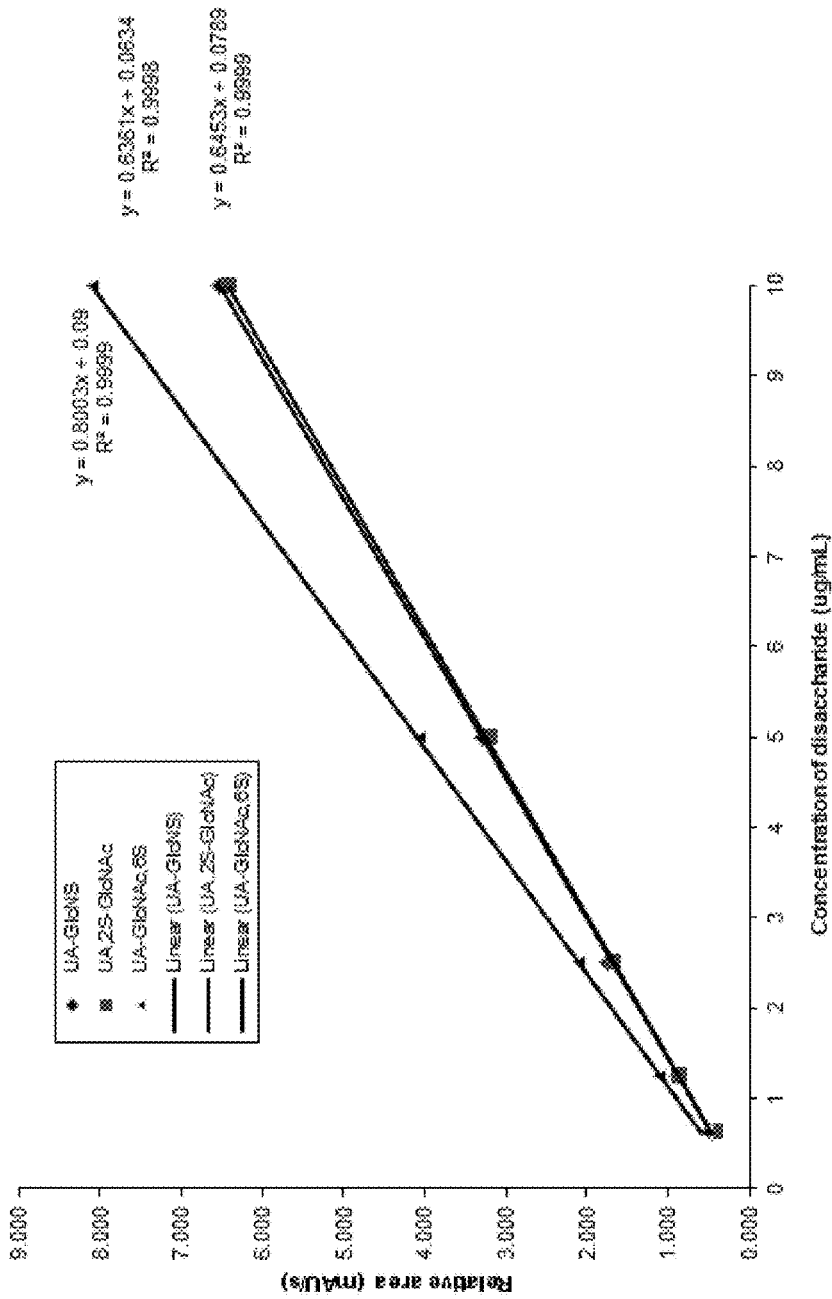
Figure 3:
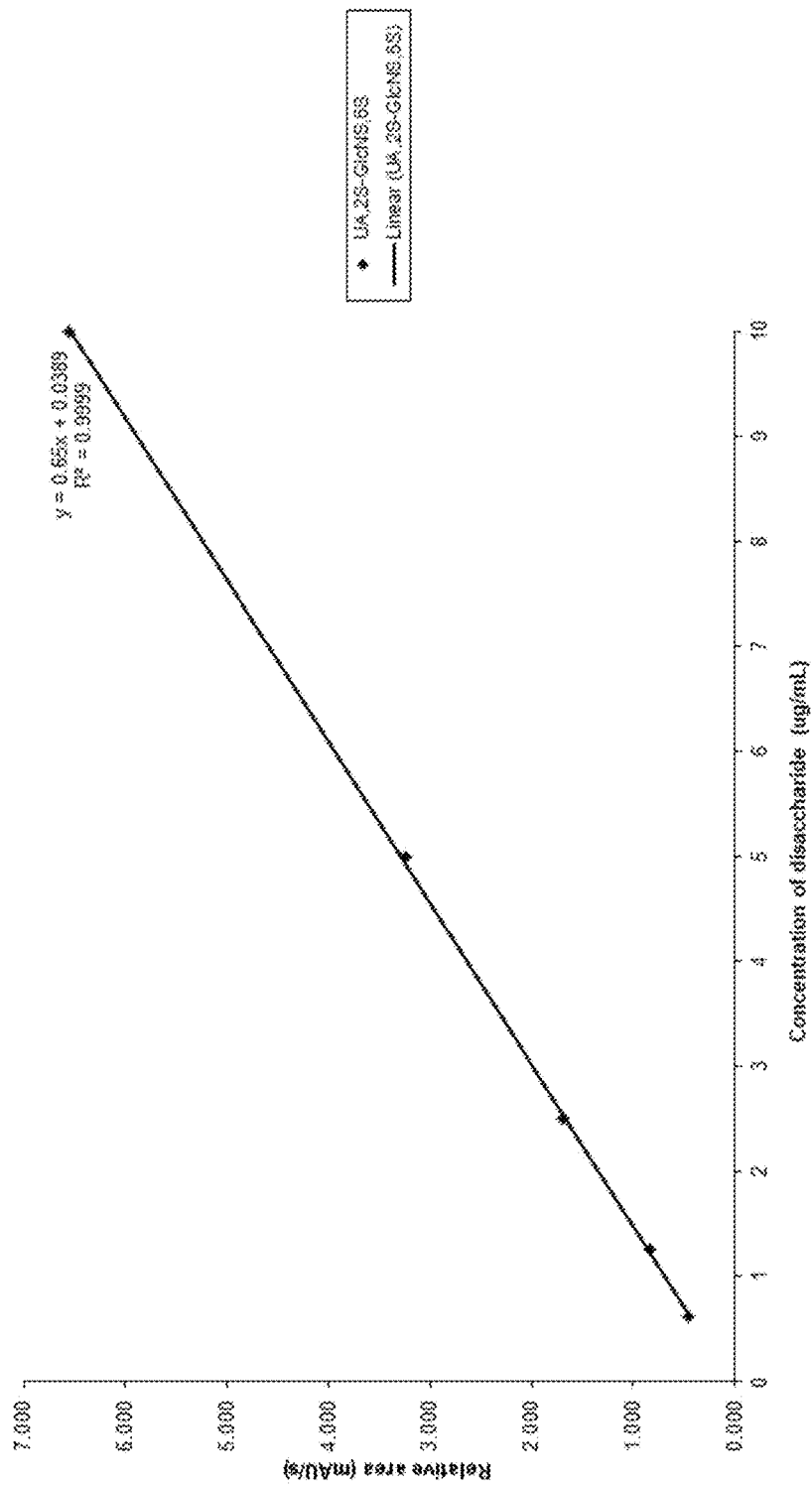

HS7 according to the present invention preferably binds $VEGF_{165}$ with significantly higher affinity than heparan sulphate from porcine mucosa (e.g. as demonstrated in Example 2 and FIG. 2A).

HS7 according to the present invention preferably induces neovascularisation in the chick chorioallantoic membrane (CAM) assay (see Example 2). In some embodiments HS7 exhibits moderately stronger pre-angiogenic efficacy in the chick chorioallantoic membrane (CAM) assay compared with $VEGF_{165}$.

Figure 4:
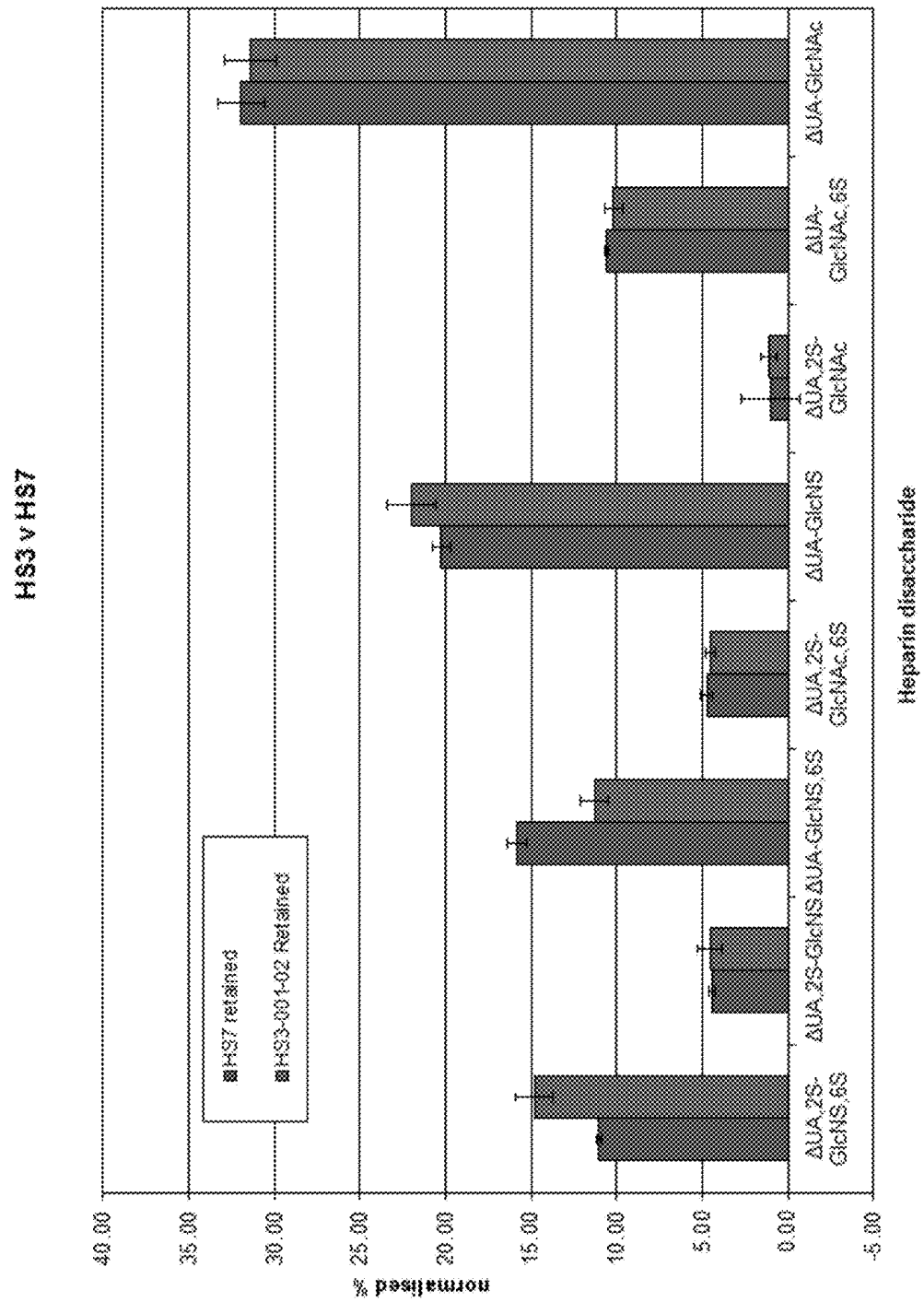
FIG. 4. Chart showing percentage disaccharide composition of HS7 (left bar) and HS3 (right bar) following digestion with heparin lyases I, II and III to completion and then subjecting the resulting disaccharide fragments to capillary electrophoresis analysis.
Figure 5:
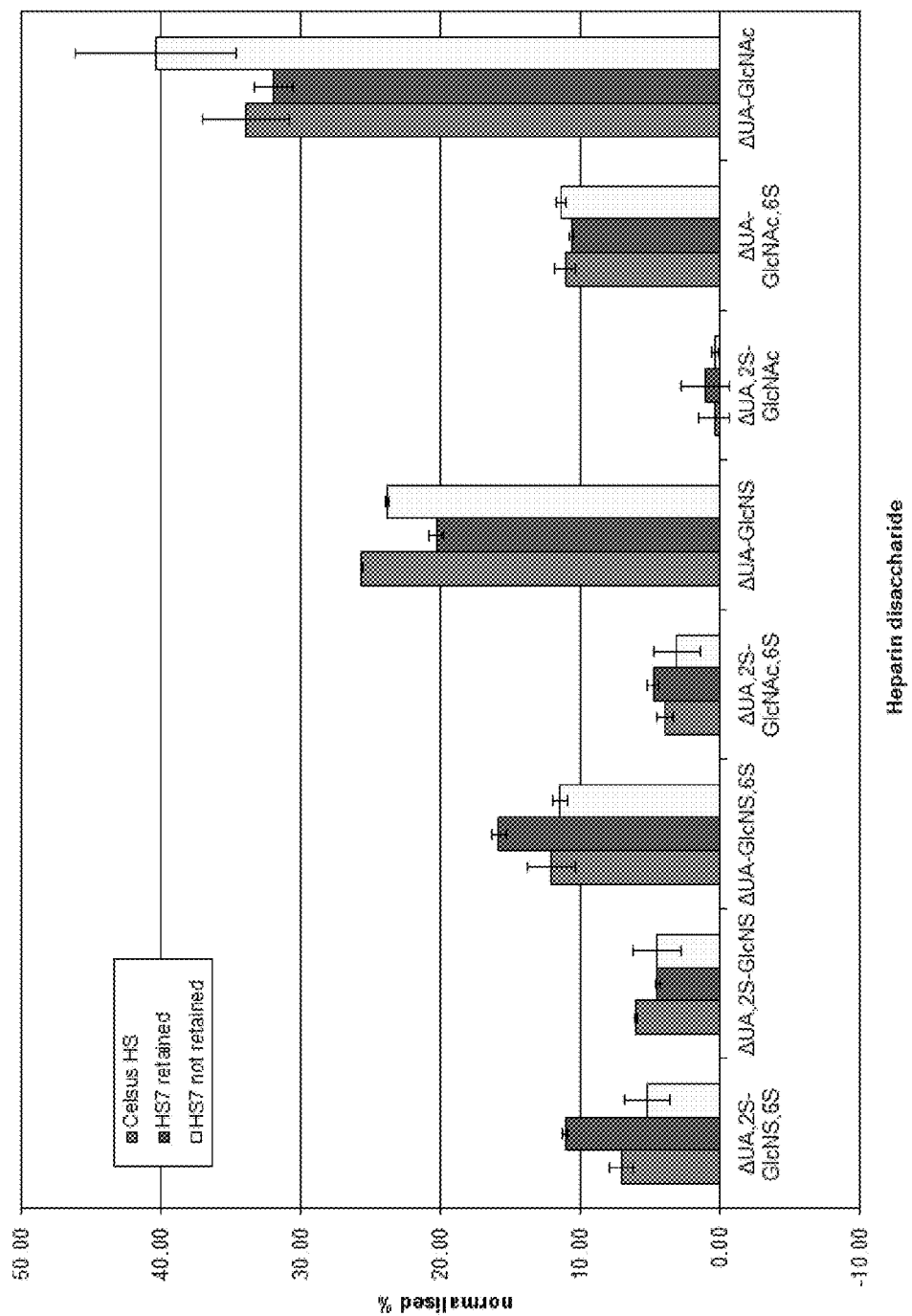
FIG. 5. Chart showing percentage disaccharide composition of Celsus HS (left bar), HS7+ (HS7 retained—middle bar) and HS7− (HS7 not retained—right bar) following digestion with heparin lyases I, II and III to completion and then subjecting the resulting disaccharide fragments to capillary electrophoresis analysis.
Figure 6:
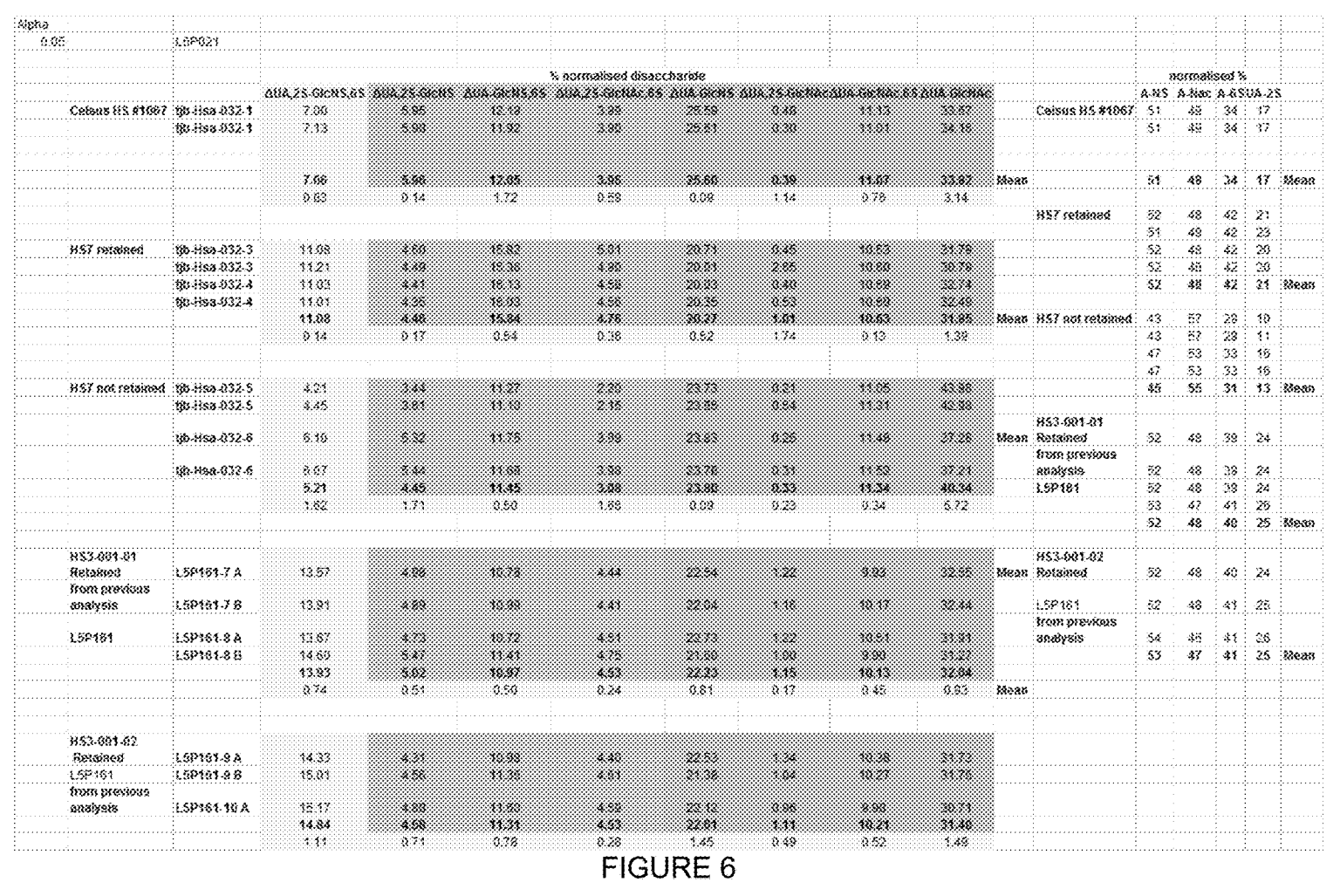

The disaccharide composition of HS7 following digestion with heparin lyases I, II and III to completion and then subjecting the resulting disaccharide fragments to capillary electrophoresis analysis is shown in FIGS. 4, 5 and 6.

HS7 according to the present invention includes heparan sulphate that has a disaccharide composition within ±10% (more preferably ±one of 9%, 8%, 7%, 6%, 5%, 4%, 3%, 2%, 1% or 0.5%) of the normalised percentage values (bold line) shown for each disaccharide in FIG. 6 for the HS7 retained species or in one of FIG. 4 or 5 for the HS7 retained species, as determined by digestion with heparin lyases I, II and III to completion and then subjecting the resulting disaccharide fragments to capillary electrophoresis analysis.

The disaccharide composition of HS7 as determined by digestion with heparin lyases I, II and III to completion and then subjecting the resulting disaccharide fragments to capillary electrophoresis analysis may have a disaccharide composition according to any one of the following:

| Disaccharide | Normalised weight percentage |
| --- | --- |
| ΔUA,2S-GlcNS,6S | 11.08 ± 3.0 |
| ΔUA,2S-GlcNS | 4.46 ± 2.0 |
| ΔUA-GlcNS,6S | 15.84 ± 3.0 |
| ΔUA,2S-GlcNAc,6S | 4.76 ± 2.0 |
| ΔUA-GlcNS | 20.27 ± 3.0 |
| ΔUA,2S-GlcNAc | 1.01 ± 0.5 |
| ΔUA-GlcNAc,6S | 10.63 ± 2.0 |
| ΔUA-GlcNAc | 31.95 ± 3.0 |
| or | |
| ΔUA,2S-GlcNS,6S | 11.08 ± 2.0 |
| ΔUA,2S-GlcNS | 4.46 ± 2.0 |
| ΔUA-GlcNS,6S | 15.84 ± 2.0 |
| ΔUA,2S-GlcNAc,6S | 4.76 ± 2.0 |
| ΔUA-GlcNS | 20.27 ± 2.0 |
| ΔUA,2S-GlcNAc | 1.01 ± 0.5 |
| ΔUA-GlcNAc,6S | 10.63 ± 2.0 |
| ΔUA-GlcNAc | 31.95 ± 2.0 |
| or | |
| ΔUA,2S-GlcNS,6S | 11.08 ± 2.0 |
| ΔUA,2S-GlcNS | 4.46 ± 1.0 |
| ΔUA-GlcNS,6S | 15.84 ± 2.0 |
| ΔUA,2S-GlcNAc,6S | 4.76 ± 1.0 |
| ΔUA-GlcNS | 20.27 ± 2.0 |
| ΔUA,2S-GlcNAc | 1.01 ± 0.5 |
| ΔUA-GlcNAc,6S | 10.63 ± 2.0 |
| ΔUA-GlcNAc | 31.95 ± 3.0 |
| or | |
| ΔUA,2S-GlcNS,6S | 11.08 ± 1.0 |
| ΔUA,2S-GlcNS | 4.46 ± 0.4 |
| ΔUA-GlcNS,6S | 15.84 ± 1.0 |
| ΔUA,2S-GlcNAc,6S | 4.76 ± 0.6 |
| ΔUA-GlcNS | 20.27 ± 3.0 |
| ΔUA,2S-GlcNAc | 1.01 ± 0.4 |
| ΔUA-GlcNAc,6S | 10.63 ± 1.0 |
| ΔUA-GlcNAc | 31.95 ± 1.6 |
| or | |
| ΔUA,2S-GlcNS,6S | 11.08 ± 0.75 |
| ΔUA,2S-GlcNS | 4.46 ± 0.3 |
| ΔUA-GlcNS,6S | 15.84 ± 0.75 |
| ΔUA,2S-GlcNAc,6S | 4.76 ± 0.45 |
| ΔUA-GlcNS | 20.27 ± 2.25 |
| ΔUA,2S-GlcNAc | 1.01 ± 0.3 |
| ΔUA-GlcNAc,6S | 10.63 ± 0.75 |
| ΔUA-GlcNAc | 31.95 ± 1.2 |
| or | |
| ΔUA,2S-GlcNS,6S | 11.08 ± 0.5 |
| ΔUA,2S-GlcNS | 4.46 ± 0.2 |
| ΔUA-GlcNS,6S | 15.84 ± 0.5 |
| ΔUA,2SGlcNAc,6S | 4.76 ± 0.3 |
| ΔUA-GlcNS | 20.27 ± 1.5 |
| ΔUA,2S-GlcNAc | 1.01 ± 0.2 |
| ΔUA-GlcNAc,6S | 10.63 ± 0.5 |
| ΔUA-GlcNAc | 31.95 ± 0.8 |

In preferred embodiments the total weight percentage of the 8 disaccharides listed is 100% (optionally ±3.0% or less, or ±2.0% or less, ±1.0% or less, ±0.5% or less).

Comparison of HS7 with an HS isolated as having high affinity for the growth factor BMP2, called HS3 (described in WO2010/030244) reveals that the structural dissimilarity of HS7 compared to HS3 is characterised by the amount of the following disaccharides: ΔUA,2S-GlcNS,6S, ΔUA-GlcNS,6S. In particular HS7 has a lower percentage composition of ΔUA,2S-GlcNS,6S than HS3 and greater percentage composition of ΔUA-GlcNS,6S than HS3. HS7 also has a slightly lower percentage composition of ΔUA-GlcNS than HS3. For example, see FIGS. 4 and 6.

As such, HS7 may be characterised by having a percentage composition of ΔUA,2S-GlcNS,6S of 11.08±1.5 or less, or ±1.0 or less, or ±0.5 or less, or ±0.25 or less. HS7 may additionally or alternatively be characterised by having a percentage composition of ΔUA-GlcNS,6S of 15.84±2.5 or less, or ±2.0 or less, or ±1.5 or less, or ±1.0 or less, or ±0.5 or less, or ±0.25 or less. HS7 may additionally or alternatively be characterised by having a percentage composition of ΔUA-GlcNS of 20.27±1.5 or less, or ±1.0 or less, or ±0.5 or less, or ±0.25 or less. In these embodiments the percentage composition of the remaining disaccharide components may be as listed above, or as shown in FIG. 6 ±one of 10%, 9%, 8%, 7%, 6%, 5%, 4%, 3%, 2%, 1% or 0.5%.

Digestion of HS7 with heparin lyases I, II and III and/or capillary electrophoresis analysis of disaccharides is preferably performed in accordance with Example 5.

Digestion of HS preparations with heparin lyase enzymes may be conducted as follows: HS preparations (1 mg) are each dissolved in 500 µL of sodium acetate buffer (100 mM containing 10 mM calcium acetate, pH 7.0) and 2.5 mU each of the three enzymes is added; the samples are incubated at 37° C. overnight (24 h) with gentle inversion (9 rpm) of the sample tubes; a further 2.5 mU each of the three enzymes is added to the samples which are incubated at 37° C. for a further 48 h with gentle inversion (9 rpm) of the sample tubes; digests are halted by heating (100° C., 5 min) and are then lyophilized; digests are resuspended in 500 µL water and an aliquot (50 µL) is taken for analysis.

Capillary electrophoresis (CE) of disaccharides from digestion of HS preparations may be conducted as follows: capillary electrophoresis operating buffer is made by adding an aqueous solution of 20 mM $H_3PO_4$ to a solution of 20 mM $Na_2HPO_4.12H_2O$ to give pH 3.5; column wash is 100 mM NaOH (diluted from 50% w/w NaOH); operating buffer and column wash are both filtered using a filter unit fitted with 0.2 µm cellulose acetate membrane filters; stock solutions of disaccharide Is (e.g. 12) are prepared by dissolving the disaccharides in water (1 mg/mL); calibration curves for the standards are determined by preparing a mix containing all standards containing 10 µg/100 µL of each disaccharide and a dilution series containing 10, 5, 2.5, 1.25, 0.625, 0.3125 µg/100 µL is prepared; including 2.5 µg of internal standard (ΔUA,2S-GlcNCOEt,6S). The digests of HS are diluted (50 µL/mL) with water and the same internal standard is added (2.5 µg) to each sample. The solutions are freeze-dried and re-suspended in water (1 mL). The samples are filtered using PTFE hydrophilic disposable syringe filter units.

Analyses are performed using a capillary electrophoresis instrument on an uncoated fused silica capillary tube at 25° C. using 20 mM operating buffer with a capillary voltage of 30 kV. The samples are introduced to the capillary tube using hydrodynamic injection at the cathodic (reverse polarity) end. Before each run, the capillary is flushed with 100 mM NaOH (2 min), with water (2 min) and pre-conditioned with operating buffer (5 min). A buffer replenishment system replaces the buffer in the inlet and outlet tubes to ensure consistent volumes, pH and ionic strength are maintained. Water only blanks are run at both the beginning, middle and end of the sample sequence. Absorbance is monitored at 232 nm. All data is stored in a database and is subsequently retrieved and re-processed. Duplicate or triplicate digests/analyses may be performed and the normalized percentage of the disaccharides in the HS digest is calculated as the mean average of the results for the analyses.

To identify HS7 the inventors enriched for glycosaminoglycan molecules that exhibit binding to particular polypeptides having a heparin-binding domain (as described in WO2010/030244, incorporated herein by reference). Isolated GAG mixtures and/or molecules can then be identified and tested for their ability to modulate the growth of blood vessels. This enables the controlled analysis of the effect of particular GAG saccharide sequences, both in vitro and in vivo. The inventors applied this methodology to VEGF in order to isolate and characterise GAGs having high binding to VEGF.

Accordingly, to identify/obtain HS7 the inventors used a method of isolating glycosaminoglycans capable of binding to a VEGF protein, the method comprising:
 (i) providing a solid support having polypeptide molecules adhered to the support, wherein the polypeptide comprises a heparin-binding domain of a VEGF protein;
 (ii) contacting the polypeptide molecules with a mixture comprising glycosaminoglycans such that polypeptide-glycosaminoglycan complexes are allowed to form;
 (iii) partitioning polypeptide-glycosaminoglycan complexes from the remainder of the mixture;
 (iv) dissociating glycosaminoglycans from the polypeptide-glycosaminoglycan complexes;
 (v) collecting the dissociated glycosaminoglycans.

The inventors also provide isolated glycosaminoglycans identified by their ability to promote or stimulate the growth of blood vessels. To do this, they provided a method of identifying glycosaminoglycans capable of promoting or stimulating the growth of blood vessels, the method comprising:
 (i) providing a solid support having polypeptide molecules adhered to the support, wherein the polypeptide comprises a heparin-binding domain of a VEGF protein;
 (ii) contacting the polypeptide molecules with a mixture comprising glycosaminoglycans such that polypeptide-glycosaminoglycan complexes are allowed to form;
 (iii) partitioning polypeptide-glycosaminoglycan complexes from the remainder of the mixture;
 (iv) dissociating glycosaminoglycans from the polypeptide-glycosaminoglycan complexes;
 (v) collecting the dissociated glycosaminoglycans;
 (vi) assaying the collected glycosaminoglycans for their ability to promote or stimulate the growth of blood vessels.

The inventors used these methods to identify a GAG capable of binding to VEGF (which they called HS7), wherein the polypeptide used in the inventors' methodology comprised the heparin-binding domain of SEQ ID NO:1.

In the inventors' methodology, the mixture comprising GAGs may contain synthetic glycosaminoglycans. However, GAGs obtained from cells or tissues are preferred. Commercially available sources of heparan sulphate, such as heparan sulphate from porcine intestinal mucosa may be used. In other examples, the mixture may contain extracellular matrix wherein the extracellular matrix material is obtained by scraping live tissue in situ (i.e. directly from the tissue in the body of the human or animal from which it is obtained) or by scraping tissue (live or dead) that has been extracted from the body of the human or animal. Alternatively, the extracellular matrix material may be obtained from cells grown in culture.

GAG mixtures may contain a mixture of different types of glycosaminoglycan, which may include dextran sulphates, chondroitin sulphates and heparan sulphates. Preferably, the GAG mixture contacted with the solid support is enriched for heparan sulphate. A heparan sulphate-enriched GAG fraction may be obtained by performing column chromatography on the GAG mixture, e.g. weak, medium or strong anion exchange chromatography, as well as strong high pressure liquid chromatography (SAX-HPLC), with selection of the appropriate fraction.

The collected GAGs may be subjected to further analysis in order to identify the GAG, e.g. determine GAG composition or sequence, or determine structural characteristics of the GAG. GAG structure is typically highly complex, and, taking account of currently available analytical techniques, exact determinations of GAG sequence structure are not possible in most cases.

However, the collected GAG molecules may be subjected to partial or complete saccharide digestion (e.g. chemically by nitrous acid or enzymatically with lyases such as heparinase III) to yield saccharide fragments that are both characteristic and diagnostic of the GAG. In particular, digestion to yield disaccharides (or tetrasaccharides) may be used to measure the percentage of each disaccharide obtained which will provide a characteristic disaccharide "fingerprint" of the GAG.

The pattern of sulphation of the GAG can also be determined and used to determine GAG structure. For example, for heparan sulphate the pattern of sulphation at amino sugars and at the C2, C3 and C6 positions may be used to characterise the heparan sulphate.

Disaccharide analysis, tetrasaccharide analysis and analysis of sulphation can be used in conjunction with other analytical techniques such as HPLC, mass spectrometry and NMR which can each provide unique spectra for the GAG. In combination, these techniques may provide a definitive structural characterisation of the GAG.

A high affinity binding interaction between the GAG and heparin-binding domain indicates that the GAG will contain a specific saccharide sequence that contributes to the high affinity binding interaction. A further step may comprise determination of the complete or partial saccharide sequence of the GAG, or the key portion of the GAG, involved in the binding interaction.

GAG-polypeptide complexes may be subjected to treatment with an agent that lyses glycosaminoglycan chains, e.g. a lyase. Lyase treatment may cleave portions of the bound GAG that are not taking part in the binding interaction with the polypeptide. Portions of the GAG that are taking part in the binding interaction with the polypeptide may be protected from lyase action. After removal of the lyase, e.g. following a washing step, the GAG molecule that remains bound to the polypeptide represents the specific binding partner ("GAG ligand") of the polypeptide. Owing to the lower complexity of shorter GAG molecules, following dissociation and collection of the GAG ligand, a higher degree of structural characterisation of the GAG ligand can be expected. For example, the combination of any of the saccharide sequence (i.e. the primary (linear) sequence of monosaccharides contained in the GAG ligand), sulphation pattern, disaccharide and/or tetrasaccharide digestion analysis, NMR spectra, mass spectrometry spectra and HPLC spectra may provide a high level of structural characterisation of the GAG ligand.

As used herein, the terms 'enriching', 'enrichment', 'enriched', etc. describes a process (or state) whereby the relative composition of a mixture is (or has been) altered in such a way that the fraction of that mixture given by one or more of those entities is increased, while the fraction of that mixture given by one or more different entities is decreased.

GAGs isolated by enrichment may be pure, i.e. contain substantially only one type of GAG, or may continue to be a mixture of different types of GAG, the mixture having a higher proportion of particular GAGs that bind to the heparin-binding domain relative to the starting mixture.

The GAGs identified preferably exhibit a functional effect when contacted with cells or tissue in which a protein containing the heparin-binding domain is expressed or contained. The functional effect may be a modulating or potentiating effect.

The functional effect may be to promote (stimulate) or inhibit the proliferation of the cells of a certain type or the differentiation of one cell type into another, or the expression of one or more protein markers. In some preferred embodiments the functional effect is the stimulation or promotion of the growth of blood vessels, including existing and/or new blood vessels.

As used herein, the term 'modulating effect' is understood to mean the effect that a first entity has on a second entity wherein the second entity's normal function in another process or processes is modified by the presence of the first entity. The modulating effect may be either agonistic or antagonistic.

The modulating effect may be a potentiating effect. The term 'potentiating effect' is understood to mean the effect of increasing potency. In a preferred embodiment of the present invention, the term 'potentiating effect' refers to the effect that a first entity has on a second entity, which effect increases the potency of that second entity in another process or processes. In a further preferred embodiment of the present invention, the potentiating effect is understood to mean the effect of isolated GAGs on a heparin-binding factor, wherein the said effect increases the potency of said heparin-binding factor.

The potentiating effect may be an increase in bioavailability of the heparin-binding factor. In a preferred embodiment of the present invention, the potentiating effect is an increase in bioavailability of VEGF. One method of measuring an increase in bioavailability of the heparin-binding factor is through determining an increase in local concentration of the heparin-binding factor.

The potentiating effect may be to protect the heparin-binding factor from degradation. In an especially preferred embodiment of the present invention, the potentiating effect is to protect VEGF from degradation. One method of determining a decrease in the degradation of the heparin-binding factor is through measuring an increase in the half-life of the heparin-binding factor.

The potentiating effect may be to sequester heparin-binding factors away from cellular receptors or may be to stabilise the ligand-receptor interaction.

The potentiating effect (e.g. modulation of growth or differentiation) may be determined by use of appropriate assays. For example, the effect that an HS has on the stability of VEGF may be determined by ELISA.

As used herein, the process of 'contacting' involves the bringing into close physical proximity of two or more discrete entities. The process of 'contacting' involves the bringing into close proximity of two or more discrete entities for a time, and under conditions, sufficient to allow a portion of those two or more discrete entities to interact on a molecular level. Preferably, as used herein, the process of 'contacting' involves the bringing into close proximity of the mixture of compounds possessing one or more GAGs and the polypeptide corresponding to the heparin-binding domain of a heparin-binding factor. Examples of 'contacting' processes include mixing, dissolving, swelling, washing. In preferred embodiments 'contact' of the GAG mixture and polypeptide is sufficient for complexes, which may be covalent but are preferably non-covalent, to form between GAGs and polypeptides that exhibit high affinity for each other.

The polypeptide may comprise the full length or near full length primary amino acid sequence of a selected protein having a heparin-binding domain. Due to folding that may occur in longer polypeptides leading to possible masking of the heparin-binding domain from the GAG mixture, it is preferred for the polypeptide to be short. Preferably, the polypeptide will have an amino acid sequence that includes the heparin-binding domain and optionally including one or more amino acids at one or each of the N- and C-terminals of the peptides. These additional amino acids may enable the addition of linker or attachment molecules to the polypeptide that are required to attach the polypeptide to the solid support.

In preferred embodiments of the inventors' methodology, in addition to the number of amino acids in the heparin-binding domain the polypeptide contains one of 1-60, 1-50, 1-40, 1-30, 1-20, more preferably 1-10, still more preferably 1-5 additional amino acids. In some embodiments the amino acid sequence of the heparin-binding domain accounts for at least 80% of the amino acids of the polypeptide, more preferably at least 90%, still more preferably at least 95%.

In order to adhere polypeptides to the surface of a solid support the polypeptides are preferably modified to include a molecular tag, and the surface of the solid support is modified to incorporate a corresponding molecular probe having high affinity for the molecular tag, i.e. the molecular tag and probe form a binding pair. The tag and/or probe may be chosen from any one of: an antibody, a cell receptor, a ligand, biotin, any fragment or derivative of these structures, any combination of the foregoing, or any other structure with which a probe can be designed or configured to bind or otherwise associate with specificity. A preferred binding pair suitable for use as tag and probe is biotin and avidin.

The polypeptide is derived from the protein of interest, which in the present case is VEGF. By "derived from" is meant that the polypeptide is chosen, selected or prepared because it contains the amino acid sequence of a heparin-binding domain that is present in the protein of interest. The amino acid sequence of the heparin-binding domain may be modified from that appearing in the protein of interest, e.g. to investigate the effect of changes in the heparin-binding domain sequence on GAG binding.

It is understood by those skilled in the art that small variations in the amino acid sequence of a particular polypeptide may allow the inherent functionality of that portion to be maintained. It is also understood that the substitution of certain amino acid residues within a peptide with other amino acid residues that are isosteric and/or isoelectronic may either maintain or improve certain properties of the unsubstituted peptide. These variations are also encompassed within the scope of the present invention. For example, the amino acid alanine may sometimes be substituted for the amino acid glycine (and vice versa) whilst maintaining one or more of the properties of the peptide. The term 'isosteric' refers to a spatial similarity between two entities. Two examples of moieties that are isosteric at moderately elevated temperatures are the iso-propyl and tert-butyl groups. The term 'isoelectronic' refers to an electronic similarity between two entities, an example being the case where two entities possess a functionality of the same, or similar, pKa.

The polypeptide corresponding to the heparin-binding domain may be synthetic or recombinant.

The solid support may be any substrate having a surface to which molecules may be attached, directly or indirectly, through either covalent or non-covalent bonds. The solid support may include any substrate material that is capable of providing physical support for the probes that are attached to the surface. It may be a matrix support. The material is generally capable of enduring conditions related to the attachment of the probes to the surface and any subsequent treatment, handling, or processing encountered during the performance of an assay. The materials may be naturally occurring, synthetic, or a modification of a naturally occurring material. The solid support may be a plastics material (including polymers such as, e.g., poly(vinyl chloride), cyclo-olefin copolymers, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads. Any other materials known in the art that are capable of having one or more functional groups, such as any of an amino, carboxyl, thiol, or hydroxyl functional group, for example, incorporated on its surface, are also contemplated.

Preferred solid supports include columns having a polypeptide immobilized on a surface of the column. The surface may be a wall of the column, and/or may be provided by beads packed into the central space of the column.

The polypeptide may be immobilised on the solid support. Examples of methods of immobilisation include: adsorption, covalent binding, entrapment and membrane confinement. In a preferred embodiment of the present invention the interaction between the polypeptide and the matrix is substantially permanent. In a further preferred embodiment of the present invention, the interaction between the peptide and the matrix is suitably inert to ion-exchange chromatography. In a preferred arrangement, the polypeptide is attached to the surface of the solid support. It is understood that a person skilled in the art would have a large array of options to choose from to chemically and/or physically attach two entities to each other. These options are all encompassed within the scope of the present invention. In a preferred arrangement, the polypeptide is adsorbed to a solid support through the interaction of biotin with streptavidin. In a representative example of this arrangement, a molecule of biotin is bonded covalently to the polypeptide, whereupon the biotin-polypeptide conjugate binds to streptavidin, which in turn has been covalently bonded to a solid support. In another arrangement, a spacer or linker moiety may be used to connect the molecule of biotin with the polypeptide, and/or the streptavidin with the matrix.

By contacting the GAG mixture with the solid support GAG-polypeptide complexes are allowed to form. These are partitioned from the remainder of the mixture by removing the remainder of the mixture from the solid support, e.g. by washing the solid support to elute non-bound materials. Where a column is used as the solid support non-binding components of the GAG mixture can be eluted from the column leaving the GAG-polypeptide complexes bound to the column.

It is understood that certain oligosaccharides may interact in a non-specific manner with the polypeptide. In certain embodiments, oligosaccharide which interacts with the polypeptide in a non-specific manner may be included in, or excluded from the mixture of compounds enriched with one or more GAGs that modulate the effect of a heparin-binding factor. An example of a non-specific interaction is the temporary confinement within a pocket of a suitably sized and/or shaped molecule. Further it is understood that these oligosaccharides may elute more slowly than those oligosaccharides that display no interaction with the peptide at all. Furthermore it is understood that the compounds that bind non-specifically may not require the input of the same external stimulus to make them elute as for those compounds that bind in a specific manner (for example through an ionic interaction). The inventors' methodology is capable of separating a mixture of oligosaccharides into those components of that mixture that: bind in a specific manner to the polypeptide; those that bind in a non-specific manner to the polypeptide; and those that do not bind to the polypeptide. These designations are defined operationally for each GAG-peptide pair.

By varying the conditions (e.g. salt concentration) present at the surface of the solid support where binding of the GAG and polypeptide occurs those GAGs having the highest affinity and/or specificity for the heparin-binding domain can be selected.

GAGs may accordingly be obtained that have a high binding affinity for a protein of interest and/or the heparin-binding domain of the protein of interest. The binding affinity ($K_d$) may be chosen from one of: less than 100 µM, less than 50 µM, less than 40 µM, less than 30 µM, less than 20 µM, less than 10 µM, less than 1 µM, less than 100 nM, less than 10 nM, less than 1 nM, less than 100 pM.

In another embodiment HS7 may be formulated for use in a method of medical treatment, including the prevention or treatment of injury or disease. A pharmaceutical composition or medicament may be provided comprising HS7 and a pharmaceutically acceptable diluent, carrier or adjuvant.

Such pharmaceutical compositions or medicaments may be provided for the prevention or treatment of injury or disease. The use of HS7 in the manufacture of a medicament for the prevention or treatment of injury or disease is also provided. Optionally, pharmaceutical compositions and medicaments according to the present invention may also contain the protein of interest (i.e. VEGF) having the heparin-binding domain to which the GAG binds.

In another aspect, the present invention provides a biological scaffold comprising HS7. In some embodiments, the biological scaffolds of the present invention may be used in methods of medical treatment. The biological scaffolds provided by the present invention include extended-release drug delivery devices, tissue valves, tissue valve leaflets, drug-eluting stents, vascular grafts, wound healing or skin grafts and orthopaedic prostheses.

In another aspect, the present invention provides HS7 for use as an adjuvant.

In another aspect, the present invention provides pharmaceutically acceptable formulations comprising a mixture of compounds comprising one or more GAGs, said mixture being enriched with respect to HS7.

In another aspect, the invention provides pharmaceutically acceptable formulations comprising:
 (i) HS7 or a mixture of compounds comprising one or more GAGs, said mixture being enriched with respect to HS7; and
 (ii) VEGF,
for separate, simultaneous or sequential administration. In a preferred embodiment the formulation comprises HS7 or the mixture of compounds comprising one or more GAGs, said mixture being enriched with respect to HS7 and VEGF in intimate admixture, and is administered simultaneously to a patient in need of treatment.

In another aspect of the present invention a kit is provided for use in the repair, or regeneration of vascular tissue, said kit comprising (i) a predetermined amount of HS7, and (ii) a predetermined amount of VEGF.

The compounds of the enriched mixtures of the present invention can be administered to a subject as a pharmaceutically acceptable salt thereof. For example, base salts of the compounds of the enriched mixtures of the present invention include, but are not limited to, those formed with pharmaceutically acceptable cations, such as sodium, potassium, lithium, calcium, magnesium, ammonium and alkylammonium. The present invention includes within its scope cationic salts, for example the sodium or potassium salts.

It will be appreciated that the compounds of the enriched mixtures of the present invention which bear a carboxylic acid group may be delivered in the form of an administrable prodrug, wherein the acid moiety is esterified (to have the form —CO2R'). The term "pro-drug" specifically relates to the conversion of the —OR' group to a —OH group, or carboxylate anion therefrom, in vivo. Accordingly, the pro-drugs of the present invention may act to enhance drug adsorption and/or drug delivery into cells. The in vivo conversion of the prodrug may be facilitated either by cellular enzymes such as lipases and esterases or by chemical cleavage such as in vivo ester hydrolysis.

Medicaments and pharmaceutical compositions according to aspects of the present invention may be formulated for administration by a number of routes, including but not limited to, injection at the site of disease or injury. The medicaments and compositions may be formulated in fluid or solid form. Fluid formulations may be formulated for administration by injection to a selected region of the human or animal body.

In this specification a patient to be treated may be any animal or human. The patient may be a non-human mammal, but is more preferably a human patient. The patient may be male or female.

Methods according to the present invention may be performed in vitro or in vivo, as indicated. The term "in vitro" is intended to encompass procedures with cells in culture whereas the term "in vivo" is intended to encompass procedures with intact multi-cellular organisms.

Glycosaminglycans

As used herein, the terms 'glycosaminoglycan' and 'GAG' are used interchangeably and are understood to refer to the large collection of molecules comprising an oligosaccharide, wherein one or more of those conjoined saccharides possess an amino substituent, or a derivative thereof. Examples of GAGs are chondroitin sulfate, keratan sulfate, heparin, dermatan sulfate, hyaluronate and heparan sulfate. Heparan sulfates are preferred embodiments of the present invention.

As used herein, the term 'GAG' also extends to encompass those molecules that are GAG conjugates. An example of a GAG conjugate is a proteoglycosaminoglycan (PGAG, proteoglycan) wherein a peptidic component is covalently bound to an oligosaccharide component.

In the present invention, it is understood that there are a large number of sources of GAG compounds including natural, synthetic or semi-synthetic. A preferred source of GAGs is biological tissue. Another preferred source of GAGs is a synthetic source. In this respect, GAGs may be obtained from the synthetic elaboration of commercially available starting materials into more complicated chemical form through techniques known, or conceivable, to one skilled in the art. An example of such a commercially available starting material is glucosamine. Another preferred source of GAGs is a semi-synthetic source. In this respect, synthetic elaboration of a natural starting material, which possesses much of the complexity of the desired material, is elaborated synthetically using techniques known, or conceivable, to one skilled in the art. Examples of such a natural starting material are chitin and dextran, and examples of the types of synthetic steps that may elaborate that starting material, into a GAG mixture suitable for use in the present invention, are amide bond hydrolysis, oxidation and sulfation. Another example of a semi-synthetic route to GAGs of the desired structure comprises the synthetic interconversion of related GAGs to obtain GAGs suitable for use in the present invention.

Heparan Sulphate (HS)

Heparan sulphate is a preferred form of glycosaminoglycan.

Heparan sulfate proteoglycans (HSPGs) represent a highly diverse subgroup of proteoglycans and are composed of heparan sulfate glycosaminoglycan side chains covalently attached to a protein backbone. The core protein exists in three major forms: a secreted form known as perlecan, a form anchored in the plasma membrane known as glypican, and a transmembrane form known as syndecan. They are ubiquitous constituents of mammalian cell surfaces and most extracellular matrices. There are other proteins such as agrin, or the amyloid precursor protein, in which an HS chain may be attached to less commonly found cores.

"Heparan Sulphate" ("Heparan sulfate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulphation at C2 of IdoA and GlcA, O-sulphation at C6 of N-sulphoglucosamine (GlcNS) and occasional 0-sulphation at C3 of GlcNS. N-deacetylation/N-sulphation, 2-O-, 6-O- and 3-O-sulphation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulfate side chains consist of alternately arranged D-glucuronic acid or L-iduronic acid and D-glucosamine, linked via (1→4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulfate groups attached to the glucosamine and the uronic acid. In contrast to heparin, heparan sulfate contains less N- and O-sulfate groups and more N-acetyl groups. The heparan sulfate side chains are linked to a serine residue of the core protein through a tetrasaccharide linkage (-glucuronosyl-β-(1→3)-galactosyl-β-(1→3)-galactosyl-β-(1→4)-xylosyl-β-1-O-(Serine)) region.

Both heparan sulfate chains and core protein may undergo a series of modifications that may ultimately influence their biological activity. Complexity of HS has been considered to surpass that of nucleic acids (Lindahl et al, 1998, J. Biol. Chem. 273, 24979; Sugahara and Kitagawa, 2000, Curr. Opin. Struct. Biol. 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), J. Biol. Chem. 273(8), 4350-4359, which is herein incorporated by reference in its entirety).

It is hypothesized that the highly variable heparan sulfate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulfate glycosaminoglycans may be genetically described (Alberts et al. (1989) Garland Publishing, Inc, New York & London, pp. 804 and 805), heparan sulfate glycosaminoglycan species isolated from a single source may differ in biological activity. As shown in Brickman et al, 1998, Glycobiology 8, 463, two separate pools of heparan sulfate glycosaminoglycans obtained from neuroepithelial cells could specifically activate either FGF-1 or FGF-2, depending on mitogenic status. Similarly, the capability of a heparan sulfate (HS) to interact with either FGF-1 or FGF-2 is described in WO 96/23003 in which a respective HS capable of interacting with FGF-1 is obtainable from murine cells at embryonic day from about 11 to about 13, whereas a HS capable of interacting with FGF-2 is obtainable at embryonic day from about 8 to about 10.

As stated above HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulfation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerisation of heparan sulphate leads to the eventual degradation of the carbohydrate chain into its individual disaccharide components when taken to completion.

For example, nitrous acid may be prepared by chilling 250 µl of 0.5 M $H_2SO_4$ and 0.5 M $Ba(NO_2)_2$ separately on ice for 15 min. After cooling, the $Ba(NO_2)_2$ is combined with the $H_2SO_4$ and vortexed before being centrifuged to remove the barium sulphate precipitate. 125 µl of $HNO_2$ was added to GAG samples resuspended in 20 µl of $H_2O$, and vortexed before being incubated for 15 min at 25° C. with occasional mixing. After incubation, 1 M $Na_2CO_3$ was added to the sample to bring it to pH 6. Next, 100 µl of 0.25 M $NaBH_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinise III cleaves sugar chains at glucuronidic linkages. The series of Heparinase enzymes (I, II and III) each display relatively specific activity by depolymerising certain heparan sulphate sequences at particular sulfation recognition sites. Heparinase I cleaves HS chains with NS regions along the HS chain. This leads to disruption of the sulphated domains. Heparinase III depolymerises HS with the NA domains, resulting in the separation of the carbohydrate chain into individual sulphated domains. Heparinase II primarily cleaves in the NA/NS "shoulder" domains of HS chains, where varying sulfation patterns are found. Note: The repeating disaccharide backbone of the heparan polymer is a uronic acid connected to the amino sugar glucosamine. "NS" means the amino sugar is carrying a sulfate on the amino group enabling sulfation of other groups at C2, C6 and C3. "NA" indicates that the amino group is not sulphated and remains acetylated.

For example, for depolymerisation in the NA regions using Heparinase III both enzyme and lyophilised HS samples are prepared in a buffer containing 20 mM Tris-HCL, 0.1 mg/ml BSA and 4 mM $CaCl_2$ at pH 7.5. Purely by way of example, Heparinase III may be added at 5 mU per 1 µg of HS and incubated at 37° C. for 16 h before stopping the reaction by heating to 70° C. for 5 min.

Di- and tetrasaccharides may be eluted by column chromatography.

Heparin-Binding Domains

Cardin and Weintraub (Molecular Modeling of Protein-Glycosaminoglycan Interactions, Arteriosclerosis Vol. 9 No. 1 January/February 1989 p. 21-32), incorporated herein in entirety by reference, describes consensus sequences for polypeptide heparin-binding domains. The consensus sequence has either a stretch of di- or tri-basic residues separated by two or three hydropathic residues terminated by one or more basic residues. Two particular consensus sequences were identified: XBBXBX [SEQ ID NO:3] and XBBBXXBX [SEQ ID NO:4] in which B is a basic residue (e.g. Lysine, Arginine, Histidine) and X is a hydropathic residue (e.g. Alanine, Glycine, Tyrosine, Serine). Heparin-binding domains are reported to be abundant in amino acids Asn, Ser, Ala, Gly, Ile, Leu and Tyr and have a low occurrence of amino acids Cys, Glu, Asp, Met, Phe and Trp.

These consensus sequences may be used to search protein or polypeptide amino acid sequences (e.g. of VEGF polypeptides) in order to identify candidate heparin-binding domain amino acid sequences which may be synthesised and tested for GAG binding.

WO 2005/014619 A2 also discloses numerous heparin-binding peptides. The contents of WO 2005/014619 A2 are incorporated herein in entirety by reference.

Medical Uses

Some aspects the present invention are concerned with the therapeutic use (human and veterinary) of HS7. The therapeutic use may involve the stimulation or promotion of the growth of blood vessels (including existing and/or new blood vessels), e.g. the promotion or stimulation of angiogenesis or vasculogenesis. This may be achieved by administering HS7 to vascular cells or to vascular tissue.

Thus, HS7 may be used to promote or augment wound healing, particularly by promoting regeneration of blood vessels and/or the vasculature, i.e. promotion of revascularisation. HS7 preferably stimulates regeneration of blood vessels following injury and contributes to improved wound healing of the vasculature.

Tissues in which injury to the vasculature may occur and which may benefit from treatment using HS7 include all tissue types of the mammalian body.

The injury, disease or condition to be treated may be any of vascular disease, cardiovascular disease, heart disease, ischemia, ischemic disease, stroke, ischemic vascular disease, myocardial infarction, a disease or condition resulting from or being characterised by decreased blood flow to tissues and/or organs due to blocked or partially blocked arteries. In some cases treatment may be required after physical injury to the patient's body to promote re-vascularisation. In some cases treatment may be required after surgery to promote re-vascularisation at or near the site of surgery, e.g. following resection.

Accordingly, HS7 and pharmaceutical compositions and medicaments comprising HS7 are provided for use in a method of treatment comprising the promotion or stimulation of the growth of blood vessels in a mammalian subject.

Treatment may comprise wound healing. The treatment may involve repair, regeneration and growth of blood vessels. HS7 facilitates repair by facilitating new blood vessel growth.

Administration of HS7 may be to tissue at or surrounding the wound or location where blood vessel growth is required. This may include administration directly to tissue in which the injury or wound has occurred. Administration may be directly to the site of injury and/or may be to a callus formed by initial healing of the wound.

Medicaments and pharmaceutical compositions according to the present invention may be formulated for administration by a number of routes. Most preferably HS7 is formulated in fluid or liquid form for injection.

In some embodiments the HS7 is formulated as a controlled release formulation, e.g. in a drug capsule for implantation at the wound site. The HS7 may be attached to, impregnated on or soaked into a carrier material (e.g. a biomaterial) such as nanofibres or biodegradable paper or textile.

Pharmaceutical compositions, medicaments, implants and prostheses comprising HS7 may also comprise VEGF. Owing to the ability of HS7 to bind VEGF, the HS7 may act as a carrier of VEGF assisting in delivery of VEGF to the wound site and maintenance of VEGF stability.

Administration is preferably in a "therapeutically effective amount", which may be sufficient to improve blood vessel growth compared to a corresponding untreated wound or injury. The actual amount administered, and rate and time-course of administration, will depend on the nature and severity of the condition to be treated. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of HS7 doses may be administered in accordance with the guidance of the prescribing medical practitioner. Purely by way of example, HS7 may be delivered in dosages of at least 1 ng/ml, more preferably at least 5 ng/ml and optionally 10 ng/ml or more. Individual HS7 dosages may be of the order less than 1 mg and greater than 1 µg, e.g. one of about 5 µg, about 10 µg, about 25 µg, about 30 µg, about 50 µg, about 100 µg, about 0.5 mg, or about 1 mg. Examples of the techniques and protocols mentioned above can be found in Remington's Pharmaceutical Sciences, 20th Edition, 2000, pub. Lippincott, Williams & Wilkins.

Biomaterials

Pharmaceutical compositions and medicaments of the invention may take the form of a biomaterial that is coated and/or impregnated with HS7. An implant or prosthesis may be formed from the biomaterial. Such implants or prostheses may be surgically implanted to assist in regeneration, restructuring and/or re-modelling of tissue, e.g. of vascular tissue or the vasculature.

HS is highly resistant to changes in tissue pH and chemical processes making it suitable for administration with implant materials.

HS7 may be applied to implants or prostheses to accelerate new tissue formation, e.g. formation of new blood vessels, at a desired location. It will be appreciated that heparan sulphates, unlike proteins, are particularly robust and have a much better ability to withstand the solvents required for the manufacture of synthetic bioscaffolds and application to implants and prostheses.

The biomaterial may be coated or impregnated with HS7. Impregnation may comprise forming the biomaterial by mixing HS7 with the constitutive components of the biomaterial, e.g. during polymerisation, or absorbing HS7 into the biomaterial. Coating may comprise adsorbing the HS7 onto the surface of the biomaterial.

The biomaterial should allow the coated or impregnated HS7 to be released from the biomaterial when administered to or implanted in the subject. Biomaterial release kinetics may be altered by altering the structure, e.g. porosity, of the biomaterial.

In addition to coating or impregnating a biomaterial with HS7, one or more biologically active molecules may be impregnated or coated on the biomaterial. For example, at least one chosen from the group consisting of: VEGF, BMP-2, BMP-4, OP-1, FGF-1, FGF-2, TGF-β1, TGF-β2, TGF-β3; collagen; laminin; fibronectin; vitronectin.

Biomaterials coated or impregnated with HS7 may be useful in both medical and veterinary purposes. It will be appreciated that the present invention may improve the quality of life of a patient or potentially extend the life of an animal, for example a valuable racehorse for use in breeding.

The biomaterial provides a scaffold or matrix support. The biomaterial may be suitable for implantation in tissue, or may be suitable for administration (e.g. as microcapsules in solution).

The implant or prosthesis should be biocompatible, e.g. non-toxic and of low immunogenicity (most preferably non-immunogenic). The biomaterial may be biodegradable such that the biomaterial degrades as tissue generation/wound healing occurs, ultimately leaving only the regenerated tissue in situ in the subject. Alternatively a non-biodegradable biomaterial may be used, e.g. to guide blood vessel regeneration over a large discontinuity and/or to act as a structural support during wound healing, with surgical removal of the biomaterial being an optional requirement after successful wound healing.

Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking.

Alternatively biomaterials may be relatively rigid structures, e.g. formed from solid materials such as plastics or biologically inert metals such as titanium.

The biomaterial may have a porous matrix structure which may be provided by a cross-linked polymer. The matrix is preferably permeable to nutrients and growth factors required for tissue growth.

Matrix structures may be formed by crosslinking fibres, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited to, biodegradable/bioresorbable polymers which may be chosen from the group of: agarose, collagen, fibrin, chitosan, polycaprolactone, poly(DL-lactide-co-caprolactone), poly(L-lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulfone, polyurethane, polyacrylonitrile, sulfonated polysulfone, polyamide, polyacrylonitrile, polymethylmethacrylate, co-polymers thereof.

Collagen is a promising material for matrix construction owing to its biocompatibility and favourable property of supporting cell attachment and function (U.S. Pat. No. 5,019,087; Tanaka, S.; Takigawa, T.; Ichihara, S. & Nakamura, T. Mechanical properties of the bioabsorbable polyglycolic acid-collagen nerve guide tube *Polymer Engineering & Science* 2006, 46, 1461-1467). Clinically acceptable collagen sponges are one example of a matrix and are well known in the art (e.g. from Integra Life Sciences).

Fibrin scaffolds (e.g. fibrin glue) provide an alternative matrix material. Fibrin glue enjoys widespread clinical application as a wound sealant, a reservoir to deliver growth factors and as an aid in the placement and securing of biological implants (Rajesh Vasita, Dhirendra S Katti. Growth factor delivery systems for tissue engineering: a materials perspective. *Expert Reviews in Medical Devices*. 2006; 3(1): 29-47; Wong C, Inman E, Spaethe R, Helgerson S. *Thromb. Haemost*. 2003 89(3): 573-582; Pandit A S, Wilson D J, Feldman D S. Fibrin scaffold as an effective vehicle for the delivery of acidic growth factor (FGF-1). *J. Biomaterials Applications*. 2000; 14(3); 229-242; DeBlois Cote M F. Doillon C J. Heparin-fibroblast growth factor fibrin complex: in vitro and in vivo applications to collagen based materials. Biomaterials. 1994; 15(9): 665-672.).

Luong-Van et al (In vitro biocompatibility and bioactivity of microencapsulated heparan sulphate *Biomaterials* 28 (2007) 2127-2136), incorporated herein by reference, describes prolonged localised delivery of HS from polycaprolactone microcapsules.

A further example of a biomaterial is a polymer that incorporates hydroxyapatite or hyaluronic acid.

Other suitable biomaterials include ceramic or metal (e.g. titanium), hydroxyapatite, tricalcium phosphate, autografts (i.e. grafts derived from the patient's tissue), or allografts (grafts derived from the tissue of an animal that is not the patient). Biomaterials may be synthetic (e.g. metal, fibrin, ceramic) or biological (e.g. carrier materials made from animal tissue, e.g. non-human mammals (e.g. cow, pig), or human).

VEGF Protein

In this specification VEGF refers to Vascular Endothelial Growth Factor, a signal protein produce by cells that stimulates vasculogenesis and angiogenesis.

In this specification reference to VEGF includes any members of the family of VEGF proteins, including types A, B, C, D and Placenta Growth Factor (PlGF). Important VEGF splice variants included herein include $VEGF_{121}$, $VEGF_{121}b$, $VEGF_{145}$, $VEGF_{165}$, $VEGF_{165}b$, $VEGF_{189}$, and $VEGF_{206}$ The amino acid sequence of VEGF165 from *Homo sapiens* from Genbank Accession No. AAM03108.1 GI:19909065 is shown below:

[SEQ ID NO: 2]
MNFLLSWVHW SLALLLYLHH AKWSQAAPMA EGGGQNHHEV

VKFMDVYQRS YCHPIETLVD IFQEYPDEIE YIFKPSCVPL

MRCGGCCNDE GLECVPTEES NITMQIMRIK PHQGQHIGEM

```
-continued
SFLQHNKCEC RPKKDRARQE NPCGPCSERR KHLFVQDPQT

CKCSCKNTDS RCKARQLELN ERTCRCDKPR R
```

The 55 amino acid peptide SEQ ID NO:1 used to identify HS7 is indicated by underline.

In this specification "VEGF protein" includes proteins having at least 70%, more preferably one of 75%, 80%, 85%, 90%, 95%, 96%, 97%, 98%, 99% or 100% sequence identity with the amino acid sequence of SEQ ID NO:2.

The VEGF protein preferably also includes a heparin binding domain having the amino acid sequence of SEQ ID NO:1, or an amino acid sequence having one of 75%, 80%, 85%, 90%, 95%, 96%, 97%, 98%, or 99% sequence identity to SEQ ID NO:1.

The VEGF protein may be from, or derived from, any animal or human, e.g. non-human animals, e.g. rabbit, guinea pig, rat, mouse or other rodent (including from any animal in the order Rodentia), cat, dog, pig, sheep, goat, cattle (including cows, e.g. dairy cows, or any animal in the order Bos), horse (including any animal in the order Equidae), donkey, and non-human primate or other non-human vertebrate organism; and/or non-human mammalian animal; and/or human.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

EXAMPLES

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

Ischemia results in the increased production of powerful, HS-binding pro-angiogenic peptide factors (particularly $VEGF_{165}$)[3,8]. By tuning the optimal delivery of VEGF-binding HS to the injury site, we aimed to sequester and protect such an endogenous VEGF, thereby amplifying the body's innate regenerative response and alleviating the need for exogenous application of VEGF.

HS avidly binds various growth factors and their synergy plays important roles in regulating cell phenotypes. However, HS expression can be gender-[16], tissue-[17] and developmentally stage-specific[18], and variations in its hyper variable sulfation pattern results in different HS/growth factor specificities within different cells. Therefore, for the purpose of promoting angiogenesis, an heparan sulphate having specific $VEGF_{165}$-binding affinity is required. We therefore purified an HS variant based on its high affinity binding to $VEGF_{165}$, and tested its ability to promote angiogenesis in vitro.

We identified a bioactive heparan sulfate sugar (called HS7) capable of facilitating new blood vessel formation, and which may be suitable for use either as a replacement or an adjunct to existing growth factor-based therapies. Specifically, HS7 can be isolated from commercially available HS stocks based on its binding to VEGF. The isolated HS is inexpensive to make, can be readily produced in large quantity and can be stored for long periods of time.

HS7 avidly binds VEGF to maximise the potent pro-angiogenic activity of this endogenous factor, and thus reduce or even replace the therapeutic administration of high-dose VEGF. Specifically, HS7 has been demonstrated to have high activating affinity for heparin-binding VEGF ($VEGF_{165}$).

Example 1—Isolation of VEGF-Binding HS

Figure 1:
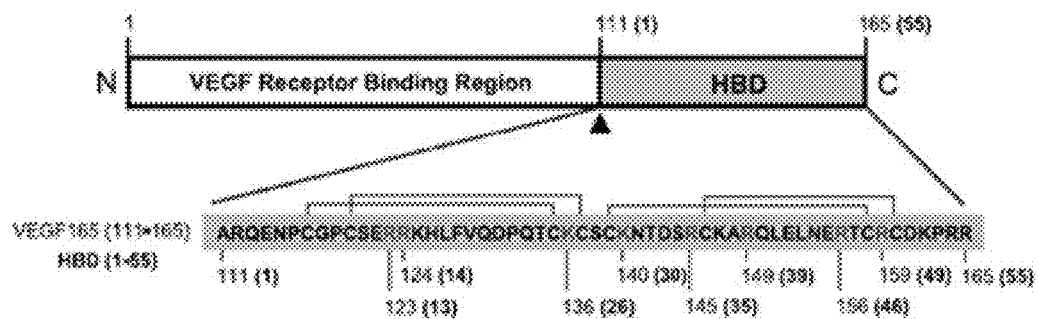
FIG. 1. (A) Schematic illustration of $VEGF_{165}$ with a 55 amino-acid heparin-binding domain at the COOH terminal, taken from ref [4]; (B) Affinity chromatography of HS7.
Figure 1:
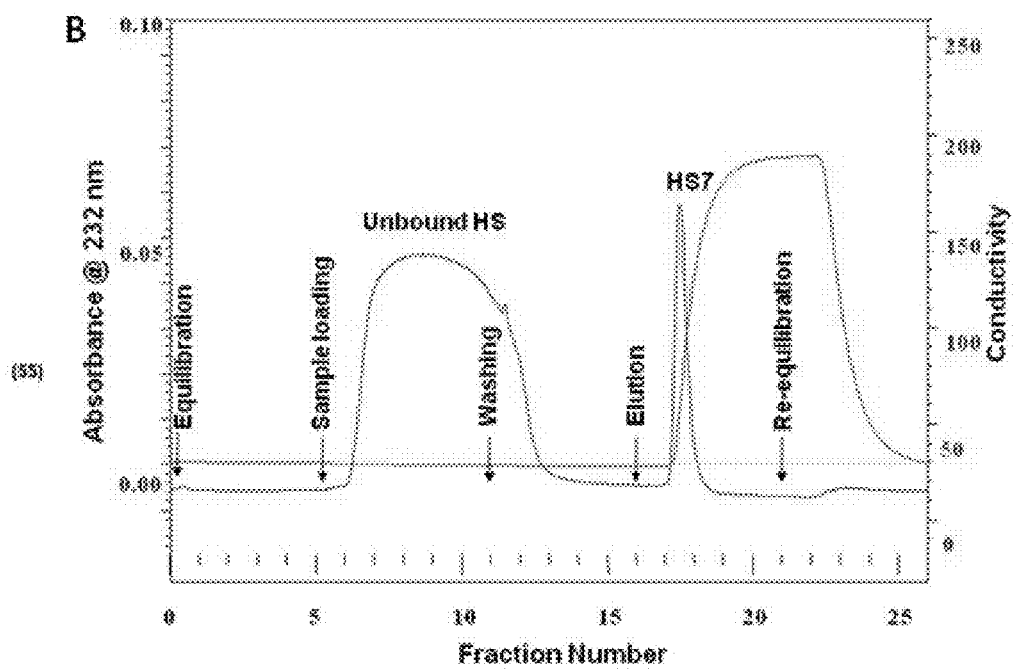

We conjugated the biotinylated heparan-binding domain of $VEGF_{165}$ (FIG. 1A) to a streptavidin column for isolating VEGF-affinity HS, so named HS7. A non-specific unbound HS ($HS^{UB}$) fraction was eluted by low salt wash buffer, and only a single peak of bound affinity-trapped HS7 retrieved by high salt elution (FIG. 1B). We managed to purify ~10 mg HS7 from 125 mg of commercially available porcine mucosal HS ($HS^C$). This proved the feasibility of acquiring a reasonable amount of VEGF-binding HS from an heterogeneous HS source.

Figure 8:
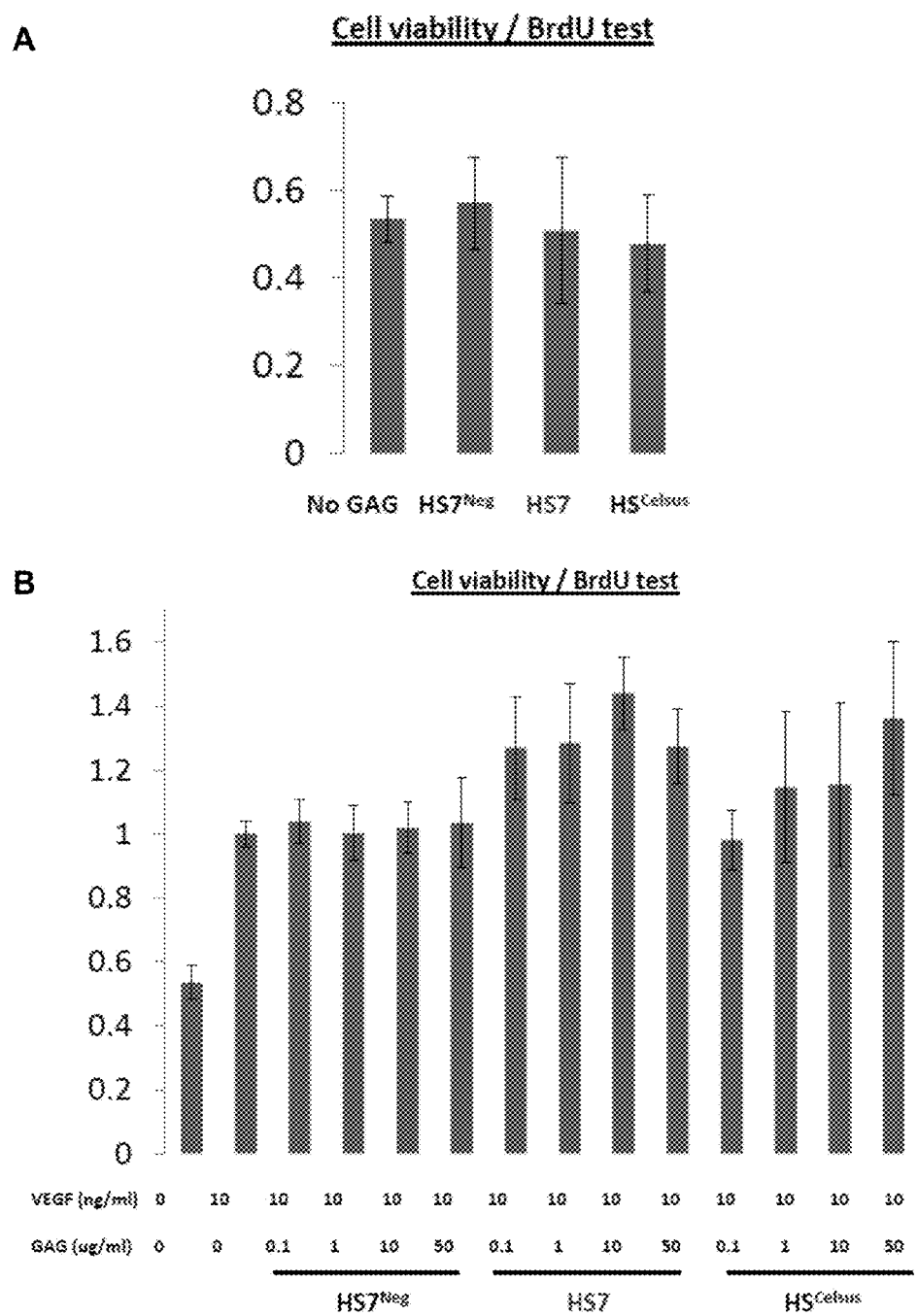
FIG. 8. HS7 promotes VEGF-mediated cell growth. (A) Chart showing cell viability of HUVEC contacted with No glycosaminoglycan (GAG), HS7−, HS7+, or Celsus HS. HS alone could not stimulate HUVEC growth. (B) Chart showing cell viability of HUVEC with No glycosaminoglycan (GAG), or varying amounts of HS7−, HS7+, or Celsus HS in combination with varying amounts of VEGF. HS7+ promotes VEGF-mediated cell growth.

Example 2—Determination of HS7 Activity in Binding VEGF and Promoting Angiogenesis We performed glycosaminoglycan enzyme-linked immunosorbant assay (GAG-ELISA) to evaluate the affinity of HS7 as compared with the crude HS material. As shown in FIG. 2A, HS7 binds significantly more $VEGF_{165}$ (218%) than does $HS^C$, proving its higher affinity to $VEGF_{165}$. Next, we utilized the chick chorioallantoic membrane (CAM) assay to determine the possible pro-angiogenic activity of HS7 alone as compared with $VEGF_{165}$ and saline controls. Both the sugar and the growth factor induced neovascularisation in the chicken embryo (FIG. 8), and HS7 exhibited moderately stronger pre-angiogenic efficacy compared with $VEGF_{165}$, suggesting that HS7 alone could effectively stimulate blood vessel formation.

Example 3—Purify and Fully Characterise VEGF165-Binding HS

We have expertise in isolating growth factor-affinitive HS species from different origins[16,19,22], and in our preliminary study the isolated HS7 (~10% yield) has shown to be active. We are now seeking to fully characterise its composition and structure. All procedures generally follow our previously well established protocols[10,16,19,20,22-24].

Affinity Chromatography of $VEGF_{165}$-Binding HS

Purification of the VEGF-binding HS fractions is based on their affinity to the heparin-binding domain of $VEGF_{165}$. Crude commercially available porcine mucosal heparan sulfate ($HS^C$) is purchased from Celsus Laboratories (Cincinnati, Ohio, USA), e.g. (e.g. INW-08-045, Heparan Sulphate I, Celsus Lab Inc, HO-03102, HO-10595, 10×100 mg.

A 55-amino acid peptide, ARQENPCGPCSER-RKHLFVQDPQTCKCSCKNTDSRCKARQLELNERT-CRCDKPRR [SEQ ID NO:1], corresponding to the heparin-binding domain of $VEGF_{165}$, is synthesised and biotinylated by ITS Science and Medical, Singapore. The peptide (5 mg) will be coupled to a streptavidin column (1 ml, GE Healthcare) according to the manufacturer's protocol. After the column is equilibrated with low salt buffer (LoSB, 20 mM PBS, 0.15 M NaCl, pH 7.2), $HS^C$ (5 mg) will be passed through the column. Isocratic flow will be kept at 1 ml/min, and all HS fractions will be monitored at 232 nm by UV detector. Unbound $HS^{UB}$ will be first collected by washing with LoSB, and the bound HS7 will further be eluted with high salt buffer (HiSB, 20 mM PBS, pH 7.2, 1.5 M NaCl). Sample peak fractions will separately be pooled and lyophilised for 48 h, and will each be tested for bioactivity on endothelial cells.

To determine whether HS7 is heterogeneous and to further fractionate it, we will also utilize a multi-step elution of HS7 using NaCl (0.5, 0.75, 1.0 and 1.5 M) at a flow rate of 0.5 ml/min. Different fractions, if determined, will be collected for further characterization and bioactivity testing.

Liquid Chromatography-Mass Spectroscopy (LC-MS)

We will treat each HS sample (5 µg) with nitrous acid for 1 h to separate di- and tetrasaccharides. Another 5 µg of each HS sample will be subjected to heparinase digestion for 16 h overnight at 37° C. to examine the resultant pattern of resistant fragments. After digestion with nitrous acid or heparinase, samples will be run on a Bio-Gel P-2 gel filtration column to determine the approximate sizes of the cleaved fragments, based on published calibrations. The disaccharide composition of the highly bioactive HS chain will be analysed by HPLC using an Agilent Prep-C18 column (10 µm, 21.2 mm×250 mm) monitored at 232 nm. Separation will be achieved by gradient elution of 0-100% solvent B (solvent A water/acetonitrile (80:20); solvent B=water/acetonitrile (35:65); tributylamine (15 mM) and ammonium acetate (50 mM) would be added to both eluents; the mobile phase pH would be adjusted to 7.0 with acetic acid) in 120 min at a flow rate of 0.5 ml/min. Molecular mass analysis will be performed using an ABI Mariner Mass Spectrometer with electrospray ionisation.

Nuclear Magnetic Resonance (NMR) Spectroscopy

The structure of each HS sample will be determined on a Bruker-Avance-600 MHz NMR spectrometer with a Bruker CryoProbe. $^1H$ and $^{13}C$ NMR spectra will be recorded followed by two-dimensional (2D) NMR spectra, COSY, NOESY, HMBC and HSQC analysis.

At the end of this experiment we will have biochemically characterised the predominant VEGF-binding HS species.

Example 4—Examine the Bioactivity of Purified HS with VEGF Binding Affinity

All procedures generally follow our well established protocols[10,16,19,20,22-24].

Heparin-Sepharose Assay

Heparin Sepharose™ 6 Fast Flow (GE Amersham) beads will be re-suspended in PBS and mixed with prepared samples of VEGF in the presence and absence of various HS samples (0.1-100 µg/ml). The mixture will be incubated at 4° C. for 15 min with shaking and thorough washing with PBS, followed by extraction of proteins with Laemmli buffer and Western blotting to determine the amount of bound VEGF.

GAG-Binding Plate ELISA

Various HS samples (5 µg/ml) will be dissolved in standard assay buffer (SAB, 100 mM NaCl, 50 mM sodium acetate, 0.2% v/v Tween 20, pH 7.2), and incubated in a 96-well GAG-binding plate (Iduron, UK) overnight. After washing and blocking, the plate will be incubated with various growth factors (including several VEGF isoforms, FGF-2, PDGF-BB, BMP-2), biotinylated primary antibody and extrAvidin-AP for 2 hr, 1 hr and 30 min, respectively, at 37° C. SigmaFast p-Nitrophenyl Reagent will be used for development followed by absorbance reading at 405 nm. This will establish the selective binding affinity that HS samples have for the tested growth factors.

Figure 7:
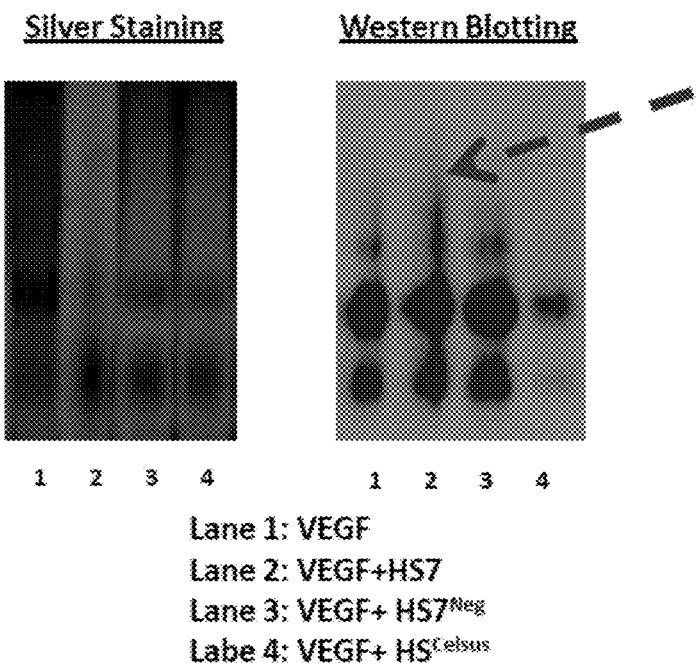
FIG. 7. HS7 has selective affinity to VEGF. (A) Photographs showing silver staining and Western blotting after Native PAGE separation—HS7 binds VEGF and decreases the mobility of VEGF after native PAGE separation. (B) Chart showing relative affinity of HS7+ for VEGF compared with crude HS (Celsus HS) and HS7−. (C) Charts showing relative affinity of HS7+ for FGF2, PDGF-BB and Endostation compared with crude HS (Celsus HS) and HS7−. HS7+ binds pro-angiogenic factors FGF2 and PDGF-BB, but has low affinity to anti-angiogenic endostatin.
Figure 7:
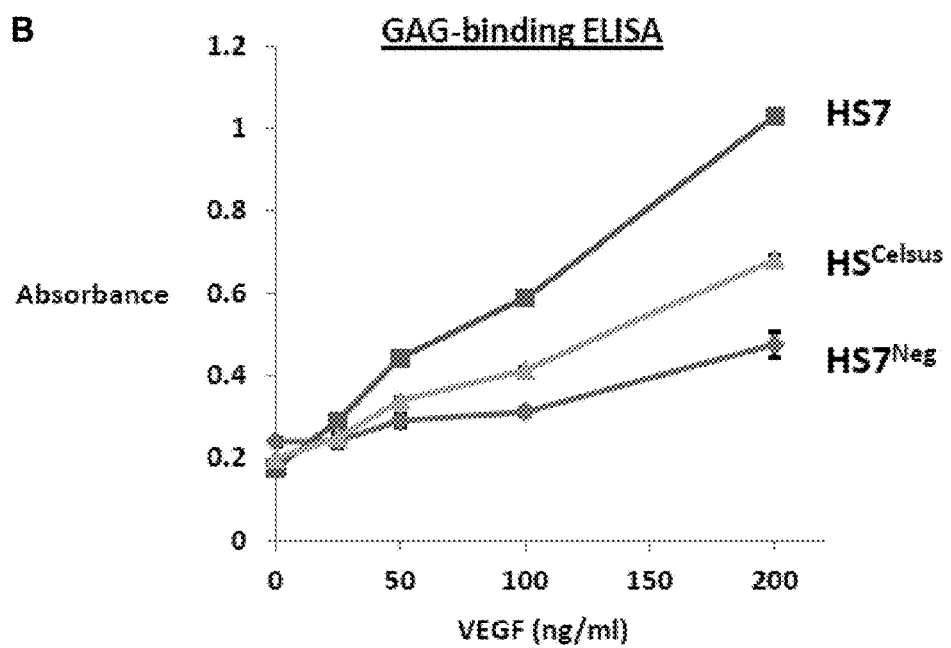
Figure 7:
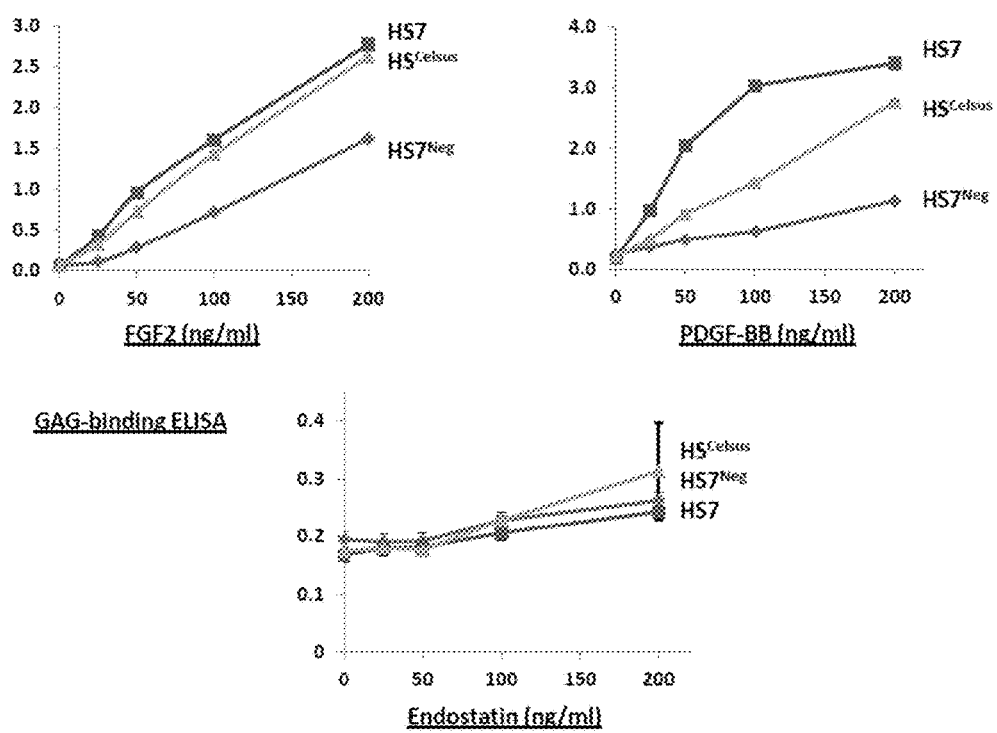

Results are shown in FIG. 7. HS7 was found to have selective affinity for VEGF, and to have higher affinity for VEGF than exhibited by Celsus HS or HS7– (FIGS. 7A and 7B). HS7 was also found to bind pro-angiogenic factors FGF-2 and PDGF-BB, but to have low affinity for the anti-angiogenic factor endostatin (FIG. 7C). Although HS7 bound FGF-2, this affinity was less compared to the affinity of both heparin and an FGF-2 binding HS variant.

Cell Culture

Human umbilical vein endothelial cells (HUVECs, EndoGRO™, SCCE001, Millipore, USA) will be maintained in EndoGRO-LS complete media kit (SCME001, Millipore) containing 2% FCS at 2,500-5,000 cells/cm$^2$ and only those in early passages will be used.

Cell Signalling Assay

After serum starvation for 24 h, HUVECs will be incubated with $VEGF_{165}$ in the presence or absence of each HS (0.1, 1, 10, and 100 µg/ml) for 5 min, 30 min and 1 h. Cells are lysed and the levels of endogenous and phosphorylated VEGFR1, VEGFR2, and ERK1/2 determined by immunoprecipitation and Western blotting.

Cell Proliferation Assay

Cells will be seeded in complete media at 3,000 cells/cm$^2$ into 24-well multi-titre (MTP) plates, incubated for 6 h for favourable cell adhesion, and serum-starved for overnight. Then, the cells would be cultured in low-serum (0.5%) media+/–$VEGF_{165}$ (5 & 10 ng/ml), $VEGF_{165}$/HSs or HSs (0.1, 1, 10, and 100 µg/ml) alone; at different time points cell number will be determined by GUAVA Viacount analysis (Millipore).

Tube Formation Assay

Type I collagen mixed with 10-fold concentrated medium 199 (Sigma) will be incubated for 1 h at 37° C. in 24 well plate to form fibrils. HUVECs will be seeded onto these gels ($5 \times 10^4$ cells/well) for 1 h, followed by removal of unattached cells. $VEGF_{165}$ (20 ng/ml), pre-mixed with different HS species (0.1-100 µg/ml), will be applied to the cells overnight, the media removed and 0.5 ml of collagen mixture will be overlaid on the cells and incubated for 1 hr at 37° C. We will use the Gen-1 Cell-based Screening System and MetaMorph® software to automatically acquire images and measure tube length as per the protocols from BD Biosciences.

Figure 10:
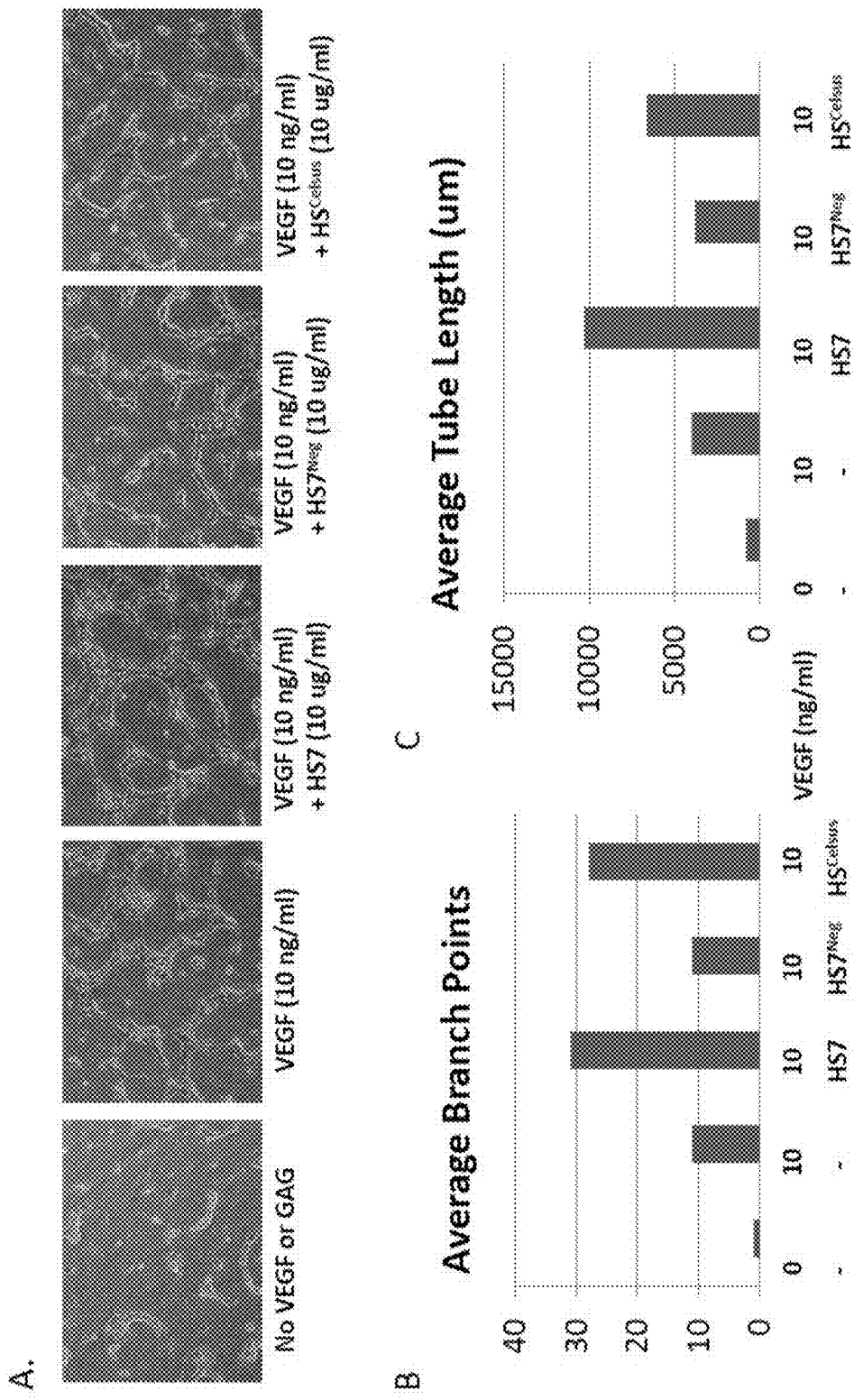
FIG. 10. HS7 enhances VEGF mediated tube formation. (A) Photographs showing tube formation in three dimensional (3D) Type I collagen matrix. (B) Chart showing average branch points. (C) Chart showing average tube length (µm).

Results are shown in FIG. 10. HS7 enhanced VEGF mediated tube formation.

Statistical Analysis

All experiments will be performed in three independent repeats. One-way ANOVA with Bonferroni post hoc testing will then be used to determine differences between treated and control cells. All statistical analysis will be performed using SPSS V 12.0 software (SPSS, Inc. Chicago, USA).

Example 5—Capillary Electrophoresis (CE) Analysis of Disaccharides

Heparan sulfate (HS) was from Celsus Laboratories Inc. (HO-03103, Lot #HO-10697). Disaccharide standards (ΔUA,2S-GlcNS,6S; ΔUA,2S-GlcNS, ΔUA,2S-GlcNAc,6S, ΔUA-GlcNS,6S, ΔUA-GlcNS, UA-GlcNAc, ΔUA,2S-GlcNAc, ΔUA-GlcNAc,6S, ΔUA,2S-GlcN, ΔUA,2S-GlcN,6S, ΔUA-GlcN,6S, ΔUA-GlcN Cat No. HD001 to HD013, Iduron Ltd, Manchester, UK), derived from the digestion of high-grade porcine heparin by bacterial heparinases, were purchased from Iduron Ltd, Manchester, UK. A synthetic derivative of a not naturally occurring disulfated disaccharide (ΔUA,2S-GlcNCOEt,6S), was also purchased from Iduron for use as an internal standard. Heparin Oligosaccharides (dp4, dp6, dp8, dp10, dp12 (Cat. No. HO04, HO06, HO08, HO10, HO12)) and selectively desulfated heparin standards (2-O, 6-O and N-desulfated heparin) (Cat No. DSH001/2, DSH002/6, DSH003/N, Iduron Ltd, Manchester, UK) were also purchased from Iduron Ltd, Manchester, UK.

Heparin lyase I (Heparitinase, EC 4.2.2.8, also known as heparitinase I), heparin lyase II (heparitinase II, no EC number assigned) and heparin lyase III (heparinase, EC 4.2.2.7, also known as heparitinase III) were obtained from Seikagaku Corporation, Japan. The enzymes, supplied as lyophilised powders (0.1 U/vial), were dissolved in 0.1% BSA to give solutions containing 0.5 mU/μL. Aliquots (5 μL; 2.5 mU) were frozen (−80° C.) until needed.

Digestion of HS Preparations with Heparin Lyase Enzymes

HS preparations (1 mg) were each dissolved in 500 μL of sodium acetate buffer (100 mM containing 10 mM calcium acetate, pH 7.0) and 2.5 mU each of the three enzymes was added. The samples were incubated at 37° C. overnight (24 h) with gentle inversion (9 rpm) of the tubes. A further 2.5 mU each of the three enzymes was added to the samples which were incubated at 37° C. for a further 48 h with gentle inversion (9 rpm) of the tubes. Digests were halted by heating (100° C., 5 min) and then lyophilized. The digests were resuspended in 500 μL water and an aliquot (50 μL) was taken for analysis by CE.

Capillary Electrophoresis (CE)

The capillary electrophoresis operating buffer was made by adding an aqueous solution of 20 mM $H_3PO_4$ to a solution of 20 mM $Na_2HPO_4.12H_2O$ to give pH 3.5. The column wash was 100 mM NaOH (diluted from 50% w/w NaOH). The operating buffer and column wash were both filtered using a Millipore filter unit fitted with 0.2 μm cellulose acetate membrane filters (47 mm ø; Schleicher and Schuell, Dassel, Germany).

Stock solutions of the 12 disaccharide standards were prepared by dissolving the disaccharides in water (1 mg/mL). To determine the calibration curves for the standards, a mix containing all twelve standards was prepared. The stock solution of the 12 standard mix contained 10 μg/100 μL of each disaccharide and a dilution series containing 10, 5, 2.5, 1.25, 0.625, 0.3125 μg/100 μL was prepared; including 2.5 μg of internal standard (ΔUA,2S-GlcNCOEt,6S). The digests of HS were diluted (50 μL/mL) with water and the same internal standard was added (2.5 μg) to each sample. The solutions were freeze-dried and re-suspended in water (1 mL). The samples were filtered using PTFE hydrophilic disposable syringe filter units (0.2 μm; 13 mm ø; Advantec, Toyo Roshi Kaisha, Ltd., Japan).

The analyses were performed using an Agilent$^{3D}$CE (Agilent Technologies, Waldbronn, Germany) instrument on an uncoated fused silica capillary tube (75 μm ID, 64.5 cm total and 56 cm effective length, Polymicro Technologies, Phoenix, Ariz., Part Number TSP075375) at 25° C. using 20 mM operating buffer with a capillary voltage of 30 kV. The samples were introduced to the capillary tube using hydrodynamic injection (50 mbar×12 sec) at the cathodic (reverse polarity) end. Before each run, the capillary was flushed with 100 mM NaOH (2 min), with water (2 min) and pre-conditioned with operating buffer (5 min). A buffer replenishment system replaced the buffer in the inlet and outlet tubes to ensure consistent volumes, pH and ionic strength were maintained. Water only blanks were run at both the beginning, middle and end of the sample sequence. Absorbance was monitored at 232 nm. All data was stored in a ChemStore database and was subsequently retrieved and re-processed using ChemStation software.

Eleven of the 12 heparin disaccharides in the standard mix were separated using conditions detailed above. The 12th disaccharide, ΔUA-GlcN, does not migrate under the conditions used for these experiments. However, this disaccharide has not been reported to occur in heparan sulfates. The $R^2$ values for the standard calibration curves ranged from 0.9949 to 1.0.

The heparin lyase I, II and III digest of the HS preparations was done in duplicate and each duplicate was injected twice in the CE. Therefore, the normalized percentage of the disaccharides in the HS digest is the mean average of the results for the analyses. Of the 11 disaccharides separated in the standard mixes, only eight of these are detected in the HS digests. Other small signals are seen on the baseline of the electrophoretograms of the digests and these may correspond to oligosaccharides >2 dp. As mentioned above, the larger oligosaccharides will have less UV absorbance compared with the disaccharides.

The proportion of the eight disaccharides in the Celsus HS digests were similar to other previous analyses with a large component of ΔUA-GlcNAc and ΔUA-GlcNS and lesser proportions of ΔUA-GlcNAc,6S, ΔUA-GlcNS,6S and ΔUA, 2S-GlcNS,6S (FIG. 5). This corresponds to the large proportion of mono- and unsulfated disaccharide lesser proportions of disulfated disaccharide and small proportion of trisulfated disaccharide consistent with the HPLC-SEC profiles. The non-retained HS is enriched in the mono- and un-sulfated disaccharides compared with the Celsus HS starting material. This pattern for the non-retained material was also seen quite distinctly in HPLC-SEC chromatograms.

Compared with HS3 (an HS isolated from Celsus HS through affinity for a heparin binding domain from BMP2) the distinctive feature of the disaccharide analysis of the HS7 preparation is the reduction of ΔUA,2S-GlcNS,6S and enrichment of ΔUA-GlcNS,6S. There is also a slight reduction in ΔUA-GlcNS (FIGS. 4 and 6).

Example 6—Native-PAGE (Polyacrylamide Gel Electrophoresis)

Methods—To examine the binding interaction between VEGF and HS, we incubated VEGF (100 ng) with HS7, HS7$^{Neg}$, or HS7$^{Celsus}$ (20 μg) at room temperature for 2 hours. Samples were separated with Native PAGE system (Invitrogen) followed by either silver staining or Western blotting analysis (FIG. 7A). For silver staining, gel was fixed overnight in 10% acetic acid and 40% ethanol solution and stained with the SilverQuest staining kit (Invitrogen); for Western blotting, the gel was transferred to pre-wetted PVDF membrane (Millipore) and blotted with anti-VEGF (1:1000, Abcam, rabbit-anti-human) and HRP-anti-rabbit secondary antibody.

Results—In FIG. 7A, a 'tail' is clearly shown with the band for VEGF incubated with HS7 (Lane 2), suggesting that binding of HS7 reduces the mobility of VEGF on the PAGE gel.

GAG-Binding ELISA

Methods—To determine the binding affinity between different HS variants with a certain growth factor, GAG-binding ELISA was performed. To each well of the GAG-binding plates (Iduron) 5 mg of various HS was added and incubated overnight. All wells were blocked with 0.25% gelatin solution, and VEGF, FGF-2, PDGF-BB, or Endostatin (25, 50, 100 and 200 ng/ml, all from R&D Systems except endostatin from Sigma) was added and incubated at 37° C. for 2 hours. Biotinylated antibodies (R&D Systems) were applied for 1 hour, ExtrAvidin-AP (Sigma) for 30 minutes, and SigmaFAST pNPP was used to develop the substrates. Measurement of absorbance was at 405 nm.

Results—As shown in FIG. 7B, HS7 has highest binding affinity to VEGF among the GAGs tested. As shown in FIG. 7C, HS7 can bind two other pro-angiogenic growth factors, namely FGF-2 and PDGF-BB; but has the minimal affinity to the anti-angiogenic factor endostatin.

Cell Proliferation Assay (BrdU Test)

Methods—Human umbilical vein endothelial cells (HUVEC) were maintained in Endo-LowSerum media kit (Millipore), and were seeded in 96 well plates with all growth factors and supplements deprived for cell proliferation tests. HS variants were incubated with VEGF for 30 minutes before being applied to cells at a final concentration of 0.1, 1, 10 and 50 ug/ml. After 24 hours, BrdU (Roche) was incorporated for 24 hours and the level of BrdU was detected by specific antibodies and substrates provided in the kit. Final reading of absorbance (450/630 nm) of each group was compared to that of the VEGF (10 ng/ml)—No GAG group.

Results—When used alone, none of the HS species could stimulate HUVEC growth (FIG. 8A). Upon pre-incubation with VEGF (10 ng/ml), the three GAG samples exert distinct effects on cell proliferation, as compared to the group with VEGF (10 ng/ml) alone and without any GAG (FIG. 8B)— (1) HS7$^{Neg}$ does not increase cell viability; (2) HS7 significantly enhances HUVEC proliferation, with HS7 at 10 µg/ml producing a highest 43% increase in cell viability; and (3) HS7$^{Celsus}$ promotes HUVEC growth to a much lower extent, with a dose of 50 µg/ml achieving ~36% increase in cell viability.

Flow Cytometry

Methods—To examine whether HS7 could facilitate VEGF binding to VEGF Receptor 2 (VEGFR2), we used a mixture of heparinase I, II, and III to treat HUVEC cultured in 6-well plates to remove endogenous HS, and applied VEGF (final concentration 20 ng/ml) pre-incubated with various HS (final concentration 20 ug/ml). Cells were collected with TrypLE (Gibco), fixed with Flow Cytometry Fixation buffer (R&D), and incubated with PE-conjugated anti-VEGF (R&D). One group of non-treated cells were stained with PE-conjugated IgG2A Isotype Control. Flow cytometry analysis was performed on the BD FACS-Array system.

Figure 9:
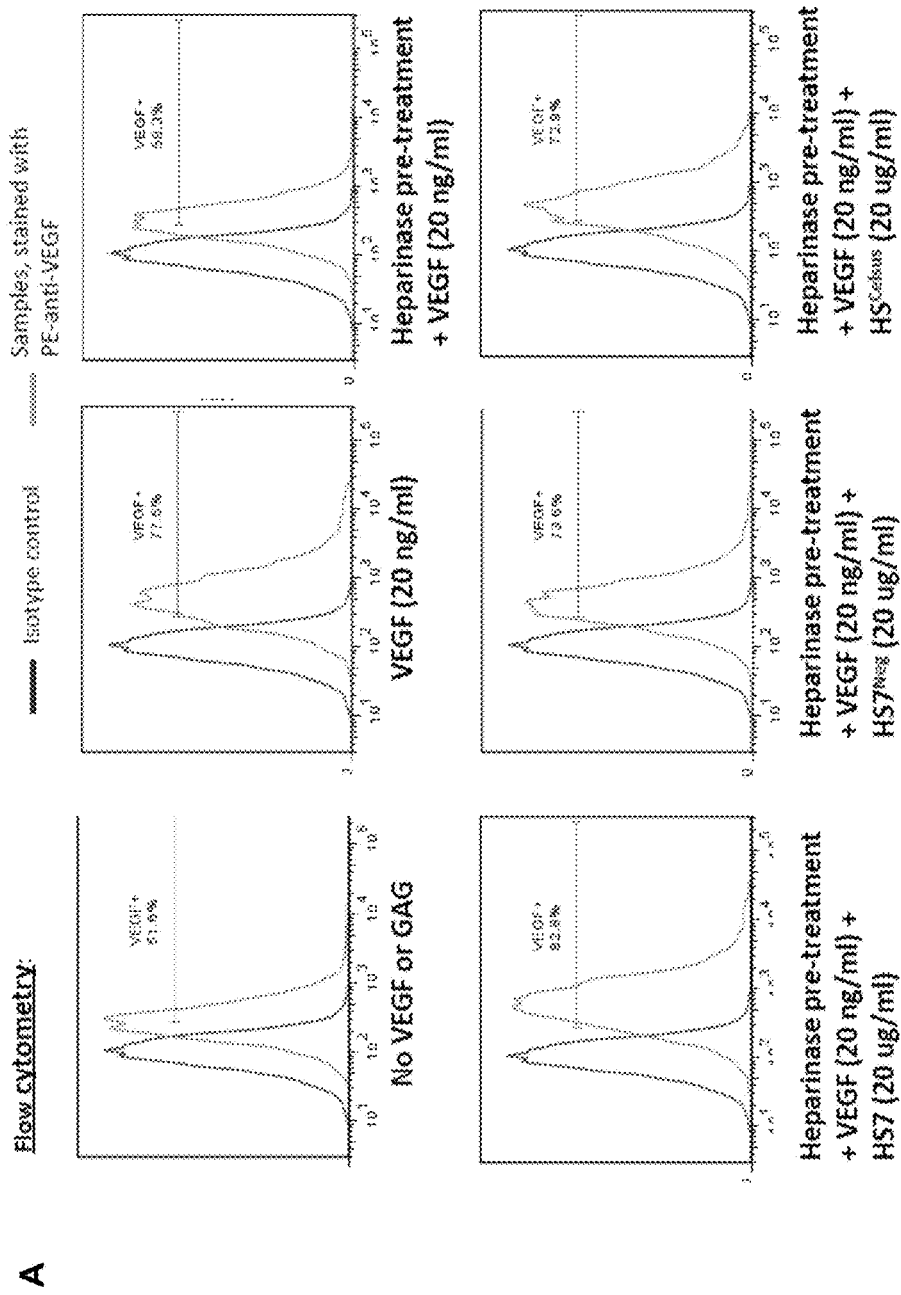
FIG. 9. HS7 facilitates VEGF-VEGFR signalling pathway. (A) Charts showing results of flow cytometry—HS7+ recovers VEGF binding on HUVEC after removal of endogenous HS. (B) Chart showing percentage of VEGF-positive cells from flow cytometry analysis. (C) Western blots showing that HS7+ recovers VEGF R2-ERK1/2 signalling after removal of endogenous HS.
Figure 9:
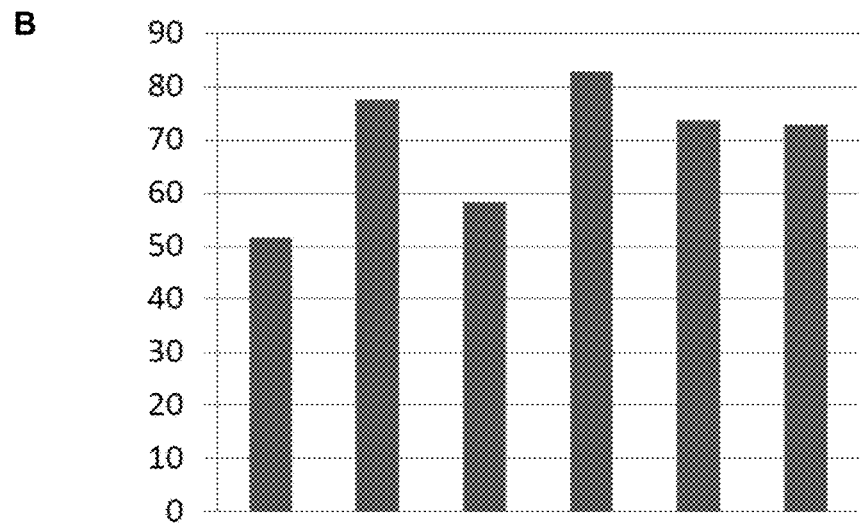
Figure 9:
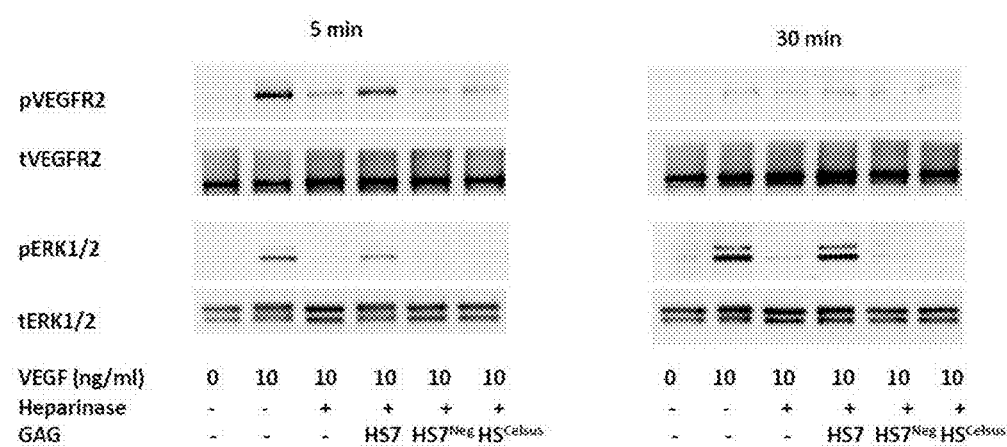

Results—As shown in FIGS. 9A and B, upon addition of exogenous VEGF to HUVEC, we detect an increase in the amount of VEGF bound to the cells from 51.6% to 77.5% (relative density compared with the isotype control). VEGF value decreases to 58.3% after enzyme treatment, suggesting removal of endogenous HS prevents VEGF from binding to its receptor. Addition of various HS species could all recover the binding to different extents—HS7 restores the value of bound VEGF to the highest at 82.8%, followed by HS7$^{Neg}$ at 73.6% and HS7$^{Celsus}$ at 72.9%, respectively.

Western Blotting

Methods—To answer whether HS7 could enhance VEGF-mediated VEGFR2-ERK1/2 signalling, we used a mixture of heparinase I, II, and III to treat HUVEC cultured in 6-well plates to remove endogenous HS, and applied VEGF (final concentration 10 ng/ml) pre-incubated with various HS (final concentration 10 ug/ml). Protein samples were collected in Laemmli buffer, separated by SDS-PAGE, and transferred to nitrocellulose membrane. Blocked with 5% BSA or milk, the membrane was incubated with primary antibodies (all from Cell Signaling Technology) against phospho-VEGFR2 (Tyr 1175), total-VEGFR2, phospho-Erk1/2 (Thr202/Tyr204), total-Erk1/2, or Cox IV as loading control and their corresponding secondary antibodies (1:10000, HRP-conjugated).

Results—It is shown in FIG. 9C that phosphorylation of VEGFR2 and ERK1/2 could be stimulated by VEGF and reduced by disruption of endogenous HS. Among the three HS species, HS7 appears to be the only one that recovers the signalling transduction.

Tube Formation

Methods—To evaluate the capability of HS7 in enhancing VEGF-mediated endothelial tube formation in 3D matrices, we seeded HUVEC in Type I collagen gels (BD Biosciences). We first prepared a solidified 'bottom layer' of collagen (0.3 ml in 24-well plate), seeded cells at $8 \times 10^4$ in 0.5 ml per well, and incubated for 2 hours. We then applied a 'top layer' of collagen (0.2 ml in 24-well plate) and after another 1 hour applied VEGF with or without HS variants. After 20 hours, 6 images were taken from each sample and were analysed by the ImageJ software to compare 'Average Branch Points' and 'Average Tube Lengths' among different groups.

Results—HUVEC supplemented with VEGF form tubular networks in the Collagen I gel matrices (FIG. 10A). The two typical parameters to judge the quality of tube formation are (i) the number of branch points and (ii) the average tubular length. Significantly more branch points are observed in both groups of VEGF+HS7, 31, and VEGF+Hs7$^{Celsus}$, 28, as compared to VEGF alone, 11 (FIG. 10B); meanwhile, the highest value of tubular length is from the VEGF+HS7 group with ~10322 µm per test, followed by the VEGF+HS7$^{Celsus}$ group with ~6631 µm per test.

Competition Assay (BrdU Test)

Methods—To examine whether HS7 exerts its activity via its binding to VEGF, we used AR55 [SEQ ID NO:1], the peptide used to generate HS7, to compete against VEGF to bind HS7. VEGF alone, VEGF incubated with HS7 for 30 minutes, and VEGF incubated with HS7 and AR55 for 30 minutes, were applied to the cells seeded and starved in 96-well plates. BrdU test was performed as described earlier.

To examine whether the activity of VEGF/HS7 is via ERK1/2 pathway, we pretreated cultured cells with U0126 (10 µM), an ERK1/2 inhibitor. VEGF/HS7 treatment and BrdU test were described above with reference to FIG. 8.

Figure 11:
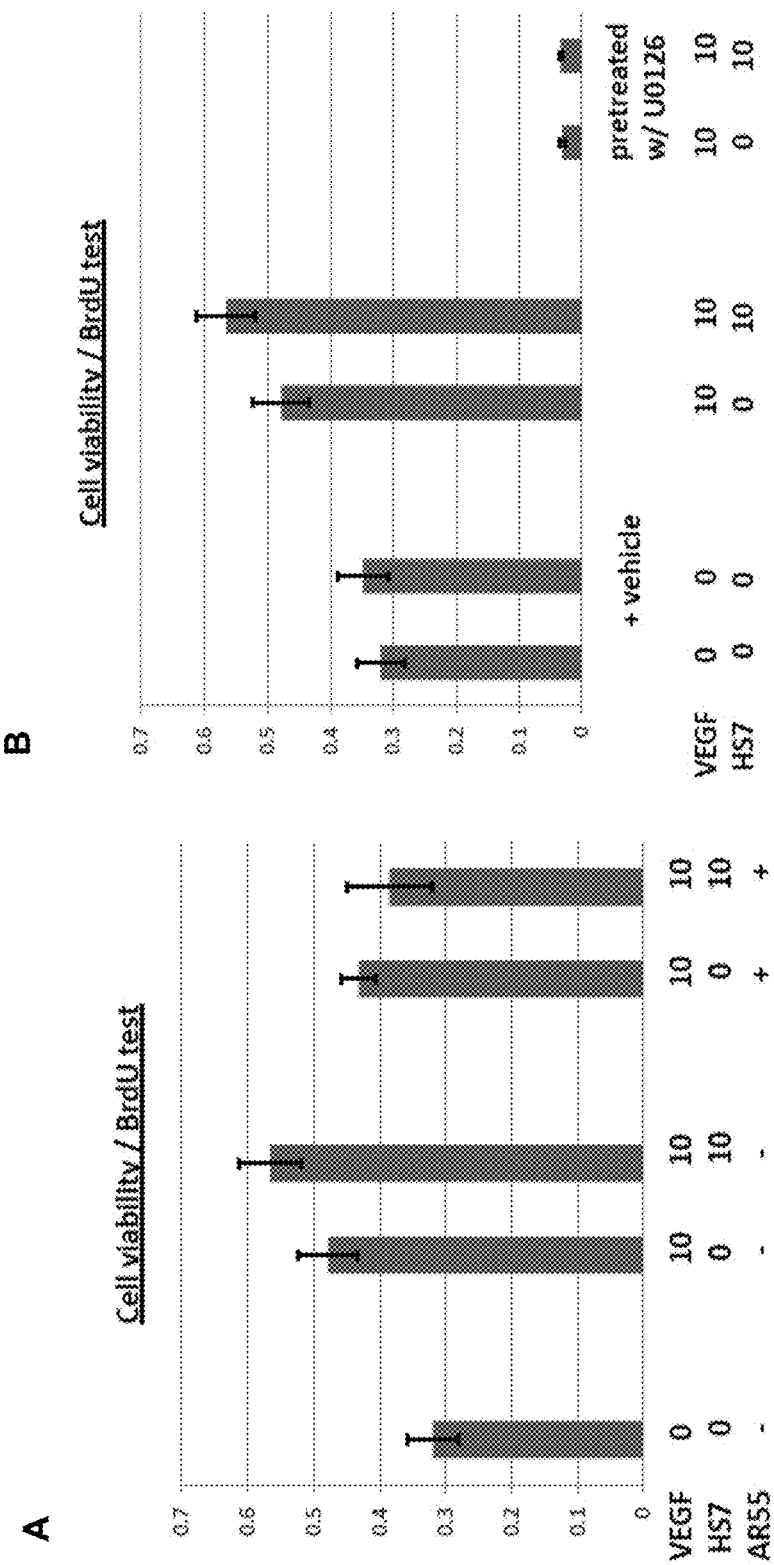
FIG. 11. Activity of HS7 is dependent on VEGF-VEGFR2 binding and ERK1/2 pathway. (A) Chart showing that the heparin-binding domain peptide, AR55, inhibits the effect of HS7. (B) Chart showing that the ERK1/2 inhibitor, UO126, completely inhibits cell growth mediated by VEGF and HS7.

Results—HS7 induces further increase in cell viability on top of VEGF stimulation; this effect is eliminated when HS7 has been pre-incubated with AR55 (FIG. 11A), suggesting that HS7 potentiates VEGF action through the binding between VEGF and the heparin-binding domain (the main peptide of AR55) of HS7. Also, inhibition of ERK1/2 disables stimulating activities of either VEGF or HS7 (FIG. 11B), confirming ERK1/2 phosphorylation plays a crucial role in VEGF/HS7 mediated cell proliferation.

Chorioallantoic Membrane (CAM) Assay

Methods—Since HS7 outperforms HS7$^{Neg}$ and HS7$^{Celsus}$ in enhancing HUVEC proliferation and tube formation in vitro, we continued to test the potential of HS7 in CAM assay that is an established in vivo model. Hatching eggs (Chew's Farm, Singapore) were incubated at 37° C., opened at Day 4 (E4) into 10-cm culture dish, and cultured ex ovo. At day 7 (E7), cut filter paper (Whatman, UK, ~2 mm in size) was placed between two main vessels. Four experimental groups—i) PBS control, ii) HS7, iii) VEGF, and (iv) HS7+VEGF—were set, and 10 µl of each sample was immediately loaded onto the paper. Photos were taken, and the final amount of HS7 per sample was 10 µg and that of VEGF was 50 ng. At day 10 (E10), photos were again taken and the formation of new vessels was compared.

Figure 12:
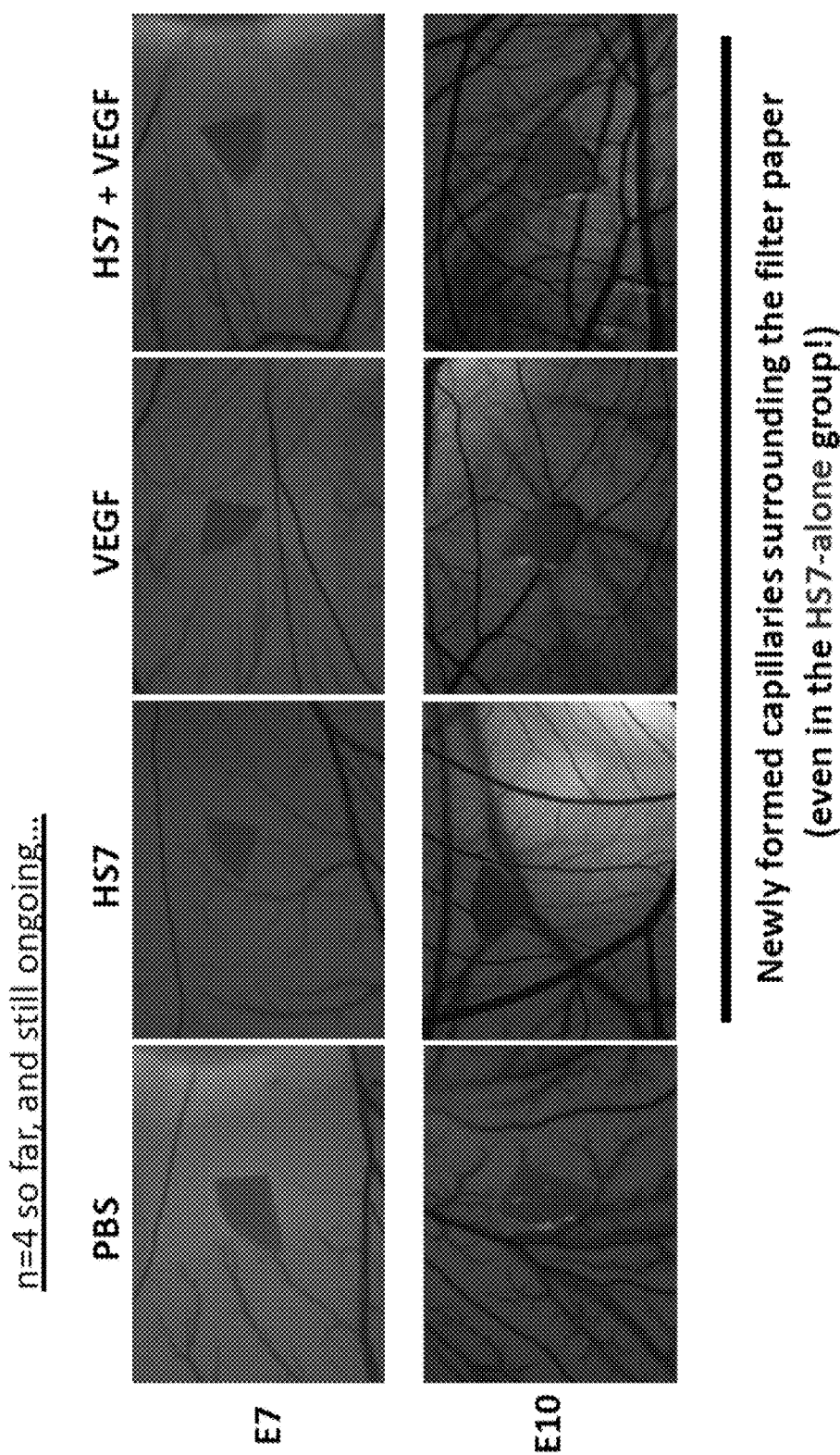
FIG. 12. Photographs showing results of chorioallantoic membrane (CAM) assay.

Results—As shown in FIG. 12, as the embryos develop, more blood vessels are observed at E10 than at E7. New capillaries formed in the PBS control group were unconnected, and were shorter and sparser than those in the other groups. Notably, in all groups except control, dense capillary vessels are observed surrounding the loaded filter papers, suggesting a strong inducing effect of both HS7 and VEGF.

Degradation Test

Methods—To examine whether HS7 could protect VEGF from degradation by plasmin, we incubated VEGF (75 ng) with HS7 (7.5 ng) in the presence (0.02 and 0.05 U/ml) or absence of plasmin at 37° C. Samples were collected after 1 hour and were directly applied to Native PAGE separation and silver staining analysis.

Figure 13:
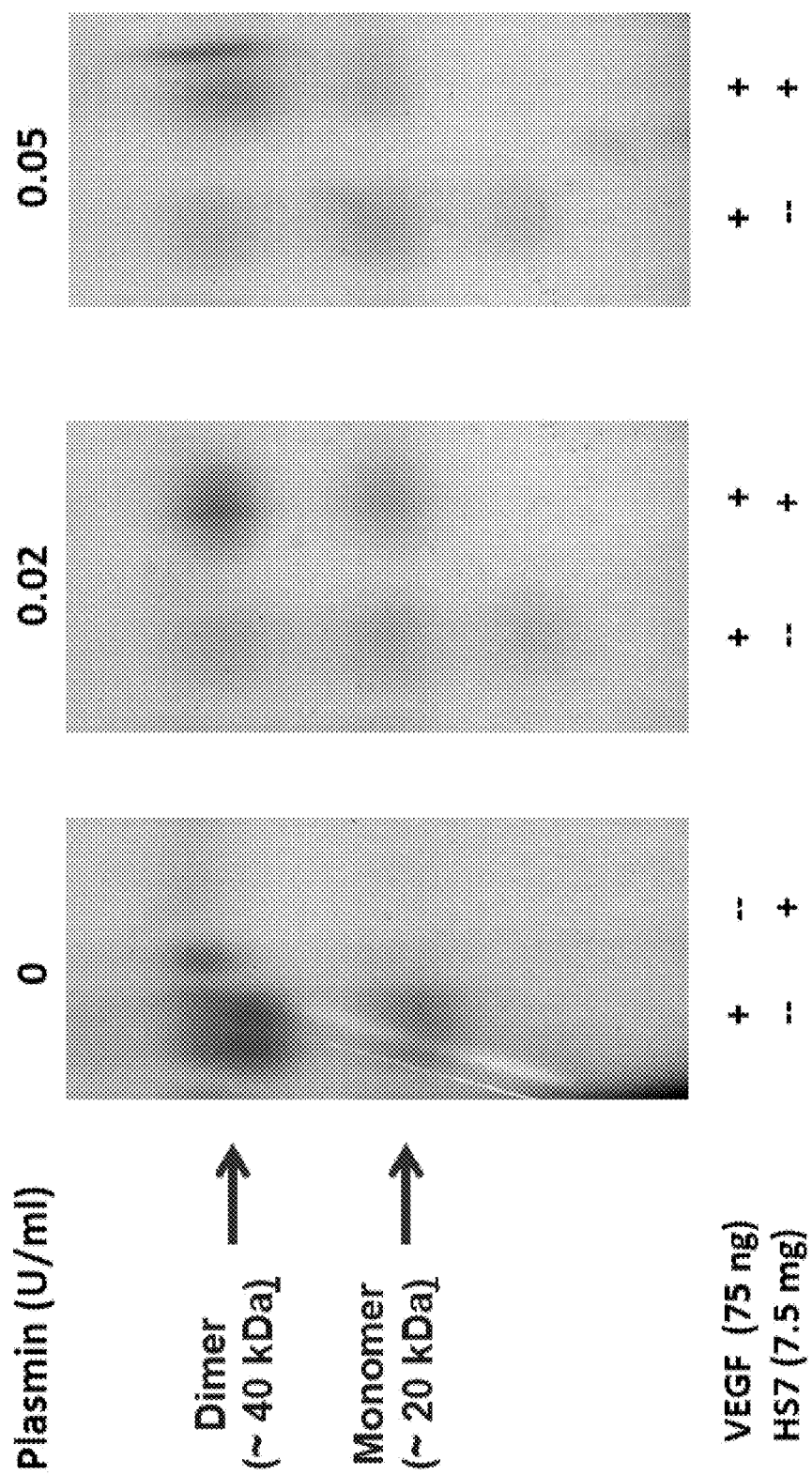
FIG. 13. Photographs of gels showing that HS7 protects VEGF from plasmin induced degradation.

Results—It is shown in FIG. 13 that recombinant VEGF is separated into two bands with native PAGE, a monomer (~20 kDa) and a dimer (~40 kDa). After treatment with plasmin at 0.02 U/ml or 0.05 U/ml for 1 hour, the two bands of VEGF appear in much higher intensity in the lane of VEGF pre-incubated with HS7 than that of VEGF alone group. This indicates that pre-incubation with HS7 could protect VEGF from plasmin cleavage.

REFERENCES

1. Singapore Heart Foundation. www.myheart.org.sg/heart-facts/statistics/. 2011. Ref Type: Generic
2. Simons, M.; Bonow, R. O.; Chronos, N. A.; Cohen, D. J.; Giordano, F. J.; Hammond, H. K.; Laham, R. J.; Li, W.; Pike, M.; Sellke, F. W.; Stegmann, T. J.; Udelson, J. E.; Rosengart, T. K. Clinical trials in coronary angiogenesis: issues, problems, consensus: An expert panel summary. Circulation 2000, 102 (11), E73-E86.
3. van der Laan, A. M.; Piek, J. J.; van, R. N. Targeting angiogenesis to restore the microcirculation after reperfused MI. Nat. Rev. Cardiol. 2009, 6 (8), 515-523.
4. Krilleke, D.; DeErkenez, A.; Schubert, W.; Giri, I.; Robinson, G. S.; Ng, Y. S.; Shima, D. T. Molecular mapping and functional characterization of the VEGF164 heparin-binding domain. J. Biol. Chem. 2007, 282 (38), 28045-28056.
5. shikari-Hada, S.; Habuchi, H.; Kariya, Y.; Kimata, K. Heparin regulates vascular endothelial growth factor165-dependent mitogenic activity, tube formation, and its receptor phosphorylation of human endothelial cells. Comparison of the effects of heparin and modified heparins. J. Biol. Chem. 2005, 280 (36), 31508-31515.
6. Xu, D.; Fuster, M. M.; Lawrence, R.; Esko, J. D. Heparan sulfate regulates VEGF165 and VEGF121-mediated vascular hyperpermeability. J. Biol. Chem. 2011, 286 (1), 737-745.
7. Wang, C.; Sun, J.; Luo, Y.; Xue, W.; Diao, H.; Dong, L.; Chen, J.; Zhang, J. A polysaccharide isolated from the medicinal herb Bletilla striata induces endothelial cells proliferation and vascular endothelial growth factor expression in vitro. Biotechnol. Lett. 2006, 28 (8), 539-543.
8. Yla-Herttuala, S.; Rissanen, T. T.; Vajanto, I.; Hartikainen, J. Vascular endothelial growth factors: biology and current status of clinical applications in cardiovascular medicine. J. Am. Coll. Cardiol. 2007, 49 (10), 1015-1026.
9. Cool, S. M.; Nurcombe, V. Heparan sulfate regulation of progenitor cell fate. J. Cell Biochem. 2006, 99 (4), 1040-1051.
10. Dombrowski, C.; Song, S. J.; Chuan, P.; Lim, X.; Susanto, E.; Sawyer, A. A.; Woodruff, M. A.; Hutmacher, D. W.; Nurcombe, V.; Cool, S. M. Heparan sulfate mediates the proliferation and differentiation of rat mesenchymal stem cells. Stem Cells Dev. 2009, 18 (4), 661-670.
11. Singh, S.; Wu, B. M.; Dunn, J. C. The enhancement of VEGF-mediated angiogenesis by polycaprolactone scaffolds with surface cross-linked heparin. Biomaterials 2011, 32 (8), 2059-2069.
12. Zieris, A.; Prokoph, S.; Levental, K. R.; Wetzel, P. B.; Grimmer, M.; Freudenberg, U.; Werner, C. FGF-2 and VEGF functionalization of starPEG-heparin hydrogels to modulate biomolecular and physical cues of angiogenesis. Biomaterials 2010, 31 (31), 7985-7994.
13. Lever, R.; Page, C. P. Novel drug development opportunities for heparin. Nat. Rev. Drug Discov. 2002, 1 (2), 140-148.
14. Dager, W. E.; Dougherty, J. A.; Nguyen, P. H.; Militello, M. A.; Smythe, M. A. Heparin-induced thrombocytopenia: treatment options and special considerations. Pharmacotherapy 2007, 27 (4), 564-587.
15. Kusmer, K. "3rd Ind. preemie infant dies of overdose". Fox News (Associated Press). www.foxnews.com/story/0,2933,214729,00.html. 20-9-0006.
Ref Type: Generic
16. Murali, S.; Leong, D. F.; Lee, J. J.; Cool, S. M.; Nurcombe, V. Comparative assessment of the effects of gender-specific heparan sulfates on mesenchymal stem cells. J. Biol. Chem. 2011, 286 (20), 17755-17765.
17. Nurcombe, V.; Cool, S. M. Heparan sulfate control of proliferation and differentiation in the stem cell niche. Crit Rev. Eukaryot. Gene Expr. 2007, 17 (2), 159-171.
18. Nurcombe, V.; Goh, F. J.; Haupt, L. M.; Murali, S.; Cool, S. M. Temporal and functional changes in glycosaminoglycan expression during osteogenesis. J. Mol. Histol. 2007, 38 (5), 469-481.
19. Murali, S.; Manton, K. J.; Tjong, V.; Su, X.; Haupt, L. M.; Cool, S. M.; Nurcombe, V. Purification and characterization of heparan sulfate from human primary osteoblasts. J. Cell Biochem. 2009, 108 (5), 1132-1142.
20. Jackson, R. A.; Nurcombe, V.; Cool, S. M. Coordinated fibroblast growth factor and heparan sulfate regulation of osteogenesis. Gene 2006, 379, 79-91.
21. Chipperfield, H.; Bedi, K. S.; Cool, S. M.; Nurcombe, V. Heparan sulfates isolated from adult neural progenitor cells can direct phenotypic maturation. Int. J. Dev. Biol. 2002, 46 (4), 661-670.
22. Manton, K. J.; Sadasivam, M.; Cool, S. M.; Nurcombe, V. Bone-specific heparan sulfates induce osteoblast growth arrest and downregulation of retinoblastoma protein. J. Cell Physiol 2006, 209 (1), 219-229.
23. Manton, K. J.; Leong, D. F.; Cool, S. M.; Nurcombe, V. Disruption of heparan and chondroitin sulfate signaling enhances mesenchymal stem cell-derived osteogenic differentiation via bone morphogenetic protein signaling pathways. Stem Cells 2007, 25 (11), 2845-2854.
24. Haupt, L. M.; Murali, S.; Mun, F. K.; Teplyuk, N.; Mei, L. F.; Stein, G. S.; van Wijnen, A. J.; Nurcombe, V.; Cool, S. M. The heparan sulfate proteoglycan (HSPG) glypican-3 mediates commitment of MC3T3-E1 cells toward osteogenesis. J. Cell Physiol 2009, 220 (3), 780-791.

We claim:

1. A method of treating vascular disease, cardiovascular disease, heart disease, ischemia, ischemic disease, stroke, ischemic vascular disease, myocardial infarction, or a disease or condition characterised by decreased blood flow to tissues or organs due to blocked or partially blocked arteries in a patient, the method comprising administration of a therapeutically effective amount of isolated or substantially purified heparan sulphate HS7 to the patient, thereby stimulating or promoting growth of blood vessels in the patient; wherein HS7 is heparan sulphate having the disaccharide composition:

| Disaccharide | Normalised weight percentage |
| --- | --- |
| ΔUA,2S-GlcNS,6S | 11.08 ± 3.0 |
| ΔUA,2S-GlcNS | 4.46 ± 2.0 |
| ΔUA-GlcNS,6S | 15.84 ± 3.0 |
| ΔUA,2S-GlcNAc,6S | 4.76 ± 2.0 |
| ΔUA-GlcNS | 20.27 ± 3.0 |
| ΔUA,2S-GlcNAc | 1.01 ± 0.5 |
| ΔUA-GlcNAc,6S | 10.63 ± 3.0 |
| ΔUA-GlcNAc | 31.95 ± 3.0 | following digestion with heparin lyases I, II and III and then subjecting the resulting disaccharide fragments to capillary electrophoresis analysis; and HS7 is heparin-free and provides high activating affinity for VEGF.

2. The method of claim 1 wherein the method comprises administering the HS7 to tissue at or surrounding a wound or location on the patient's body at which blood vessel growth is required.

3. The method of claim 1 wherein the method further comprises administering VEGF protein to the patient.

4. A method of treating a vascular disease, cardiovascular disease, heart disease, ischemia, ischemic disease, stroke, ischemic vascular disease, myocardial infarction, or a disease or condition characterised by decreased blood flow to tissues or organs due to blocked or partially blocked arteries in a patient, the method comprising surgically implanting a biocompatible implant or prosthesis, which implant or prosthesis comprises a biomaterial and HS7, into tissue of the patient at or surrounding the wound or location at which blood vessel growth is required, wherein HS7 is heparan sulphate having the disaccharide composition:

| Disaccharide | Normalised weight percentage |
| --- | --- |
| ΔUA,2S-GlcNS,6S | 11.08 ± 3.0 |
| ΔUA,2S-GlcNS | 4.46 ± 2.0 |
| ΔUA-GlcNS,6S | 15.84 ± 3.0 |
| ΔUA,2S-GlcNAc,6S | 4.76 ± 2.0 |
| ΔUA-GlcNS | 20.27 ± 3.0 |
| ΔUA,2S-GlcNAc | 1.01 ± 0.5 |
| ΔUA-GlcNAc,6S | 10.63 ± 3.0 |
| ΔUA-GlcNAc | 31.95 ± 3.0 | following digestion with heparin lyases I, II and III and then subjecting the resulting disaccharide fragments to capillary electrophoresis analysis; and HS7 is heparin-free and provides high activating affinity for VEGF.

5. A method comprising administering isolated or substantially purified HS7 to vascular cells or vascular tissue in vivo, wherein growth of blood vessels is promoted.

6. The method of claim 5 wherein the HS7 has the disaccharide composition:

| Disaccharide | Normalised weight percentage |
| --- | --- |
| ΔUA,2S-GlcNS,6S | 11.08 ± 3.0 |
| ΔUA,2S-GlcNS | 4.46 ± 2.0 |

-continued

| Disaccharide | Normalised weight percentage |
| --- | --- |
| ΔUA-GlcNS,6S | 15.84 ± 3.0 |
| ΔUA,2S-GlcNAc,6S | 4.76 ± 2.0 |
| ΔUA-GlcNS | 20.27 ± 3.0 |
| ΔUA,2S-GlcNAc | 1.01 ± 0.5 |
| ΔUA-GlcNAc,6S | 10.63 ± 3.0 |
| ΔUA-GlcNAc | 31.95 ± 3.0 | following digestion with heparin lyases, I, II and III and then subjecting the resulting disaccharide fragments to capillary electrophoresis analysis.

7. The method of claim 1 wherein the HS7 is capable of binding SEQ ID NO:1 or 2.

8. The method of claim 1 wherein the HS7 is obtained by a method comprising:
   (i) providing a solid support having polypeptide molecules adhered to the support, wherein the polypeptide comprises a heparin-binding domain having the amino acid sequence of SEQ ID NO:1;
   (ii) contacting the polypeptide molecules with a mixture comprising glycosaminoglycans such that polypeptide-glycosaminoglycan complexes are allowed to form;
   (iii) partitioning polypeptide-glycosaminoglycan complexes from the remainder of the mixture;
   (iv) dissociating glycosaminoglycans from the polypeptide-glycosaminoglycan complexes; and
   (v) collecting the dissociated glycosaminoglycans.

9. The method of claim 8, wherein the mixture comprising glycosaminoglycans is a heparan sulphate preparation obtained from porcine mucosa.

10. The method of claim 4 wherein the HS7 is capable of binding SEQ ID NO:1 or 2.

11. The method of claim 4 wherein the HS7 is obtained by a method comprising:
   (i) providing a solid support having polypeptide molecules adhered to the support, wherein the polypeptide comprises a heparin-binding domain having the amino acid sequence of SEQ ID NO:1;
   (ii) contacting the polypeptide molecules with a mixture comprising glycosaminoglycans such that polypeptide-glycosaminoglycan complexes are allowed to form;
   (iii) partitioning polypeptide-glycosaminoglycan complexes from the remainder of the mixture;
   (iv) dissociating glycosaminoglycans from the polypeptide-glycosaminoglycan complexes; and
   (v) collecting the dissociated glycosaminoglycans.

12. The method of claim 11, wherein the mixture comprising glycosaminoglycans is a heparan sulphate preparation obtained from porcine mucosa.

13. The method of claim 5 wherein the HS7 is capable of binding SEQ ID NO:1 or 2.

14. The method of claim 5 wherein the HS7 is obtained by a method comprising:
   (i) providing a solid support having polypeptide molecules adhered to the support, wherein the polypeptide comprises a heparin-binding domain having the amino acid sequence of SEQ ID NO:1;
   (ii) contacting the polypeptide molecules with a mixture comprising glycosaminoglycans such that polypeptide-glycosaminoglycan complexes are allowed to form;
   (iii) partitioning polypeptide-glycosaminoglycan complexes from the remainder of the mixture;
   (iv) dissociating glycosaminoglycans from the polypeptide-glycosaminoglycan complexes; and
   (v) collecting the dissociated glycosaminoglycans.

15. The method of claim 14, wherein the mixture comprising glycosaminoglycans is a heparan sulphate preparation obtained from porcine mucosa.

* * * * *

SEQUENCE LISTING

<160> NUMBER OF SEQ ID NOS: 4

<210> SEQ ID NO 1
<211> LENGTH: 55
<212> TYPE: PRT
<213> ORGANISM: Homo sapiens

<400> SEQUENCE: 1

Ala Arg Gln Glu Asn Pro Cys Gly Pro Cys Ser Glu Arg Arg Lys His
1               5                   10                  15

Leu Phe Val Gln Asp Pro Gln Thr Cys Lys Cys Ser Cys Lys Asn Thr
            20                  25                  30

Asp Ser Arg Cys Lys Ala Arg Gln Leu Glu Leu Asn Glu Arg Thr Cys
        35                  40                  45

Arg Cys Asp Lys Pro Arg Arg
    50                  55

<210> SEQ ID NO 2
<211> LENGTH: 191
<212> TYPE: PRT
<213> ORGANISM: Homo sapiens

<400> SEQUENCE: 2

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
            85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
            165                 170                 175

Leu Glu Leu Asn Glu Arg Thr Cys Arg Cys Asp Lys Pro Arg Arg
        180                 185                 190

<210> SEQ ID NO 3
<211> LENGTH: 6
<212> TYPE: PRT
<213> ORGANISM: Artificial sequence
<220> FEATURE:
<223> OTHER INFORMATION: Synthetic sequence: Consensus sequence
<220> FEATURE:
<221> NAME/KEY: VARIANT
<222> LOCATION: (1, 4, 6)
<223> OTHER INFORMATION: Xaa is a hydropathic residue (e.g. Alanine, Glycine, Tyrosine, Serine)
<220> FEATURE:

-continued

```
<221> NAME/KEY: VARIANT
<222> LOCATION: (2..3, 5)
<223> OTHER INFORMATION: Xaa is a basic residue (e.g. Lysine, Arginine,
      Histidine)

<400> SEQUENCE: 3

Xaa Xaa Xaa Xaa Xaa Xaa
1               5

<210> SEQ ID NO 4
<211> LENGTH: 8
<212> TYPE: PRT
<213> ORGANISM: Artificial sequence
<220> FEATURE:
<223> OTHER INFORMATION: Synthetic sequence: Consensus sequence
<220> FEATURE:
<221> NAME/KEY: VARIANT
<222> LOCATION: (1, 5..6, 8)
<223> OTHER INFORMATION: Xaa is a hydropathic residue (e.g. Alanine,
      Glycine, Tyrosine, Serine)
<220> FEATURE:
<221> NAME/KEY: VARIANT
<222> LOCATION: (2..4, 7)
<223> OTHER INFORMATION: Xaa is a basic residue (e.g. Lysine, Arginine,
      Histidine)

<400> SEQUENCE: 4

Xaa Xaa Xaa Xaa Xaa Xaa Xaa Xaa
1               5
```